United States Patent
Ryu et al.

(10) Patent No.: US 11,198,908 B2
(45) Date of Patent: *Dec. 14, 2021

(54) METHOD FOR DIAGNOSIS OF ALZHEIMER'S DISEASE USING MICRORNA

(71) Applicant: BIORCHESTRA Co., Ltd., Daejeon (KR)

(72) Inventors: Jin-Hyeob Ryu, Daejeon (KR); Hyun-Jeong Cho, Daejeon (KR)

(73) Assignee: Biorchestra Co., Ltd., Daejeon (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/443,705

(22) Filed: Jun. 17, 2019

(65) Prior Publication Data

US 2020/0392576 A1 Dec. 17, 2020

(51) Int. Cl.
| | |
|---|---|
| *C12N 15/113* | (2010.01) |
| *C12Q 1/6876* | (2018.01) |
| *G01N 33/68* | (2006.01) |
| *C12N 15/11* | (2006.01) |

(52) U.S. Cl.
CPC .......... *C12Q 1/6876* (2013.01); *C12N 15/111* (2013.01); *G01N 33/6896* (2013.01); *C12N 2310/14* (2013.01); *C12N 2310/141* (2013.01); *C12Q 2600/112* (2013.01); *C12Q 2600/178* (2013.01); *G01N 2333/4709* (2013.01); *G01N 2800/2814* (2013.01)

(58) Field of Classification Search
CPC ............ C12N 15/111; C12N 2310/141; C12N 2310/14; C12N 2310/113; C12N 2310/315; C12N 15/113
See application file for complete search history.

(56) References Cited

U.S. PATENT DOCUMENTS

| | | |
|---|---|---|
| 5,475,096 A | 12/1995 | Gold et al. |
| 5,506,097 A | 4/1996 | Potter et al. |
| 5,532,219 A | 7/1996 | McGeer et al. |
| 5,580,737 A | 12/1996 | Polisky et al. |
| 5,660,985 A | 8/1997 | Pieken et al. |
| 5,705,337 A | 1/1998 | Gold et al. |
| 6,136,861 A | 10/2000 | Chenard |
| 8,129,515 B2 | 3/2012 | Esau et al. |
| 8,754,203 B2 | 6/2014 | Tuschl et al. |
| 10,844,380 B1 * | 11/2020 | Ryu .................. A61P 25/28 |
| 2009/0004667 A1 | 1/2009 | Zichi et al. |
| 2009/0098549 A1 | 4/2009 | Schneider et al. |
| 2009/0246136 A1 | 10/2009 | Williams et al. |
| 2012/0065248 A1 | 3/2012 | Brown et al. |
| 2012/0172416 A1 | 7/2012 | Velin et al. |
| 2014/0120545 A1 | 5/2014 | Umansky et al. |
| 2016/0273043 A1 | 9/2016 | Umanksy et al. |
| 2021/0123051 A1 | 4/2021 | Ryu et al. |

FOREIGN PATENT DOCUMENTS

| | | |
|---|---|---|
| EP | 2436784 B1 | 9/2013 |
| KR | 20120088009 A | 8/2012 |
| KR | 20130140528 A | 12/2013 |
| KR | 20140025978 A | 3/2014 |
| KR | 20150095349 A | 8/2015 |
| WO | WO 2013045652 A1 | 4/2013 |
| WO | WO 2015025995 A1 | 2/2015 |
| WO | WO-2016044929 A1 | 3/2016 |
| WO | WO-2018139759 A1 | 8/2018 |
| WO | WO-2018139819 A1 | 8/2018 |

OTHER PUBLICATIONS

Watts and Corey (Journal of Pathology (2012) 226:365-379). (Year: 2012).*
English translation of WO2018139819, published 2018, retrieved from patentscope (patentscope.wipo.int) Jan. 2021 (Year: 2018).*
Bartus, R.T., et al., "The Cholinergic Hypothesis of Geriatric Memory Dysfunction," Science, 217(4558):408-417, American Association for the Advancement of Science, United States (Jul. 1982).
Carell, T., et al., A Novel Procedure for the Synthesis of Libraries Containing Small Organic Molecules, Angewandte Chemie International Edition, 33(20):2059-2061, VCH Verlagsgesellschaft, Germany (Nov. 1994).
Carell, T., et al., "A Solution Phase Screening Procedure for the Isolation of Active Compounds From a Library of Molecules," Angewandte Chemie International Edition, 33:2061-2064, VCH Verlagsgesellschaft, Germany (Nov. 1994).
Cho, C.Y., et al., "An unnatural biopolymer," Science 261(5126):1303-1305, American Association for the Advancement of Science, United States (Sep. 1993).
Coyle, J.T., et al., "Alzheimer's Disease: a Disorder of Cortical Cholinergic Innervation," Science, 219 (4589):1184-1190, American Association for the Advancement of Science, United States (Mar. 1983).
Dewitt, S.H., et al., "Diversomers: an approach to nonpeptide, nonoligomeric chemical diversity," Proceedings of the National Academy of Sciences 90(15):6909-6913, National Academy of Sciences, United States (Apr. 1993).

(Continued)

Primary Examiner — J. E. Angell
(74) Attorney, Agent, or Firm — Sterne, Kessler, Goldstein & Fox P.L.L.C.

(57) ABSTRACT

The present disclosure relates to a method for diagnosing or providing information for diagnosing Alzheimer's disease or a brain disease, and a composition and a diagnostic kit for diagnosing Alzheimer's disease or a brain disease using miR-485-3p. The present disclosure enables objective data analysis of the diagnosis of Alzheimer's disease or a brain disease by measuring the expression level of miR-485-3p in blood, minimizes risk to a patient by measuring the concentration of amyloid beta 42 in saliva, and enables quick and accurate diagnosis. Accordingly, the present disclosure is very useful for preventing Alzheimer's disease or a brain disease.

19 Claims, 10 Drawing Sheets

Specification includes a Sequence Listing.

(56) References Cited

OTHER PUBLICATIONS

Erb, E., et al., "Recursive deconvolution of combinatorial chemical libraries," Proceedings of the National Academy of Sciences 91(24):11422-11426, National Academy of Sciences, United States (Nov. 1994).
Gallop, M.A., et al., "Applications of combinatorial technologies to drug discovery. 1. Background and peptide combinatorial libraries," Journal of Medicinal Chemistry 37(9):1233-1251, American Chemical Society, United States (Apr. 1994).
Hanson, L.R., et al., "Intranasal Administration of CNS Therapeutics to Awake Mice," Journal of Visualized Experiments, (74): e4440, MYJoVE Corporation, United States (Apr. 2013).
International Search Report for Application No. PCT/KR2017/014749, dated Mar. 22, 2018, 4 pages.
Kaminska, B., et al., "Kainate-evoked Modulation of Gene Expression in Rat Brain," Acta Biochimica Polonica, 44(4):781-789, Panstwowe Wydawnictwo Naukowe, Poland (Oct. 1997).
Khachaturian Z.S., "Diagnosis of Alzheimer's Disease," Archives of Neurology, 42(11):1097-1105, American Medical Association, United States (Nov. 1985).
Kiriazis, H and Kranias, E.G. et al., "Genetically Engineered Models with Alterations in Cardiac Membrane Calcium-handling Proteins," Annual Review of Physiology, 62:321-351, Annual Reviews, United States (Feb. 2000).
Krenz. M and Robbins, J., "Impact of Beta-myosin Heavy Chain Expression on Cardiac Function During Stress," Journal of the American College of Cardiology, 44(12), pp. 2390-2397, Elsevier Biomedical, United States (Dec. 2004).
Leggio, L., et al., "Micrornas In Parkinson's Disease: From Pathogenesis to Novel Diagnostic And Therapeutic Approaches," International Journal of Molecular Sciences, 18(12): E2698, MDPI, Switzerland (Dec. 2017).
Lustig, Y., et al., "'RNA Walk' a Novel Approach to Study RNA-RNA Interactions Between a Small RNA and Its Target," Nucleic Acids Research, 38 (1):e5, Oxford University Press, England (Jan. 2010).
Piganeau, N., et al., "A Yeast RNA-hybrid System for the Detection of RNA-RNA Interactions in Vivo," RNA, 12(1):177-184, Cold Spring Harbor Laboratory Press, United States (Jan. 2006).
Seibenhener, M.L and Wooten, M.W., "Isolation and Culture of Hippocampal Neurons From Prenatal Mice," Journal of Visualized Experiments: JoVE, (65): e3634, MYJoVE Corporation, United States (Jul. 2012).
Wang, W.X., et al., "Patterns of Microrna Expression in Normal and Early Alzheimer's disease Human Temporal Cortex: White Matter Versus Gray Matter," Acta Neuropathologica, 121(2):193-205, Springer Verlag, Germany (Feb. 2011).
Zuckermann, R.N., et al., "Discovery of nanomolar ligands for 7-transmembrane G-protein-coupled receptors from a diverse N-(substituted)glycine peptoid library," Journal of Medicinal Chemistry 37(17):2678-2685, ACS Publications, United Kingdom (Aug. 1994).
Burgos, K., et al., "Profiles of Extracellular miRNA in Cerebrospinal Fluid and Serum from Patients with Alzheimer's and Parkinson's Disease Correlate with Disease Status and Features of Pathology," PLoS One 9(5):e94839, Public Library of Science, United States (May 2014).
Cardo, L.F., et al., "MiRNA profile in the substantia nigra of Parkinson's disease and healthy subjects," J Mol Neurosci 54(4):830-836, Springer Link, United States (Oct. 2014).
Chen, L., et al., "Identification of aberrant circulating miRNAs in Parkinson's disease plasma samples," Brain Behav, 8(4):e00941, Wiley Periodicals, United States (Jun. 2018).
Ebrahimkhani, S., et al., "Exosomal microRNA signatures in multiple sclerosis reflect disease status," 7:14293, Nature Publishing Group, United Kingdom (Oct. 2017).
Goh, S.Y., et al., "Role of MicroRNAs in Parkinson's Disease," Int J. Mol Sci 20(22):5649, MDPI, Switzerland (Nov. 2019).

Gu, J., et al., "MiR-485-3p modulates neural stem cell differentiation and proliferation via regulating TRIP6 expression," J Cell Mol Med. 24(1):398-404, Wiley, United States (Aug. 2019).
Gui, Y., et al., "Altered microRNA profiles in cerebrospinal fluid exosome in Parkinson disease and Alzheimer disease," Oncotarget 6(35):37043-37053, Impact Journals, United States (Oct. 2015).
Khoo, S.K., et al., "Plasma-based circulating MicroRNA biomarkers for Parkinson's disease," J Parkinsons Dis 2(4):321-331, IOS Press, Netherlands (2012).
Lau, P., et al., "Alteration of the microRNA network during the progression of Alzheimer's disease," EMBO Mol Med 5:1613, John Wiley and Sons, United States (Sep. 2013).
Marti, E., et al., "A myriad of miRNA variants in control and Huntington's disease brain regions detected by massively parallel sequencing," Nucleo Acids Res. 38(20):7219-7235, Oxford University Press, United Kingdom (Jun. 2010).
Martinez, B., et al., "MicroRNAs in Parkinson's disease and emerging therapeutic targets," Neural Regen Res 12(12):1945-1959, Publishing House of Neural Regeneration Research, China (Dec. 2017).
Nair, V.D., et al., "Alterations of miRNAs reveal a dysregulated molecular regulatory network in Parkinson's disease striatum," Neurosci Lett 629:99-104, Elsevier, Netherlands (Jun. 2016).
Rani., A., et al., "miRNA in Circulating Microvesicles as Biomarkers for Age-Related Cognitive Decline," Frontiers in Aging Neuroscience 9: 323, Frontiers Media SA, United States (Oct. 2017).
Ravandis, S., et al., "Circulating Brain-enriched MicroRNAs for detection and discrimination of idiopathic and genetic Parkinson's disease," Movement Disorders: 11 pg., Wiley Online Library, United States (Dec. 2019).
Shigemizu, D., et al., "Risk prediction models for dementia constructed by supervised principal component analysis using miRNA expression data," Communications Biology 2(77): 8 pg, Nature Publishing Group, United Kingdom (Feb. 2019).
Sorensen, S.S., et al., "miRNA expression profiles in cerebrospinal fluid and blood of patients with Alzheimer's disease and other types of dementia—an exploratory study," Transl Neurodegener 5(6):1-12, Cross Mark, United States (Mar. 2016).
Tan, L., et al., "Genome-Wide serum microRNA expression profiling identifies serum biomarkers for Alzheimer's disease," Journal Alzheimer's Disease 40(4):1017-1027, IOS Press, Netherlands (May 2014).
Weinberg, R.B., et al., "Evidence for a Neuroprotective microRNA pathway in amnestic mild cognitive impairment," Frontiers in Neuroscience 9:430, Frontiers Media SA, United States (Nov. 2015).
Co-Pending U.S. Appl. No. 16/443,700, inventors Ryu; JH, et al., filed Jun. 17, 2019. (Unpublished).
International Search Report and Written Opinion for International Application No. PCT/KR2013/007701, Korean Intellectual Property Office, Republic of Korea, dated Jul. 3, 2014, 20 pages.
Hu, K. et al., "MicroRNA expression profile of the hippocampus in a rat model of temporal lobe epilepsy and miR-34a-targeted neuroprotection against hippocampal neurone cell apoptosis post-status epilepticus," BMC Neuroscience 13:115, BioMed Central, England (Sep. 2012).
Hwang, J. et al., "Epigenetic Mechanisms in Stroke and Epilepsy," Neuropsychology Reviews 38: 167-82, American College of Neuropsychopharmacology, United States ( Jan. 2013).
Wei, F. et al., "MicroRNAs in Neural Cell Development and Brain Diseases," Science China Life Sciences 54(12):1103-12, Springer Nature, Switzerland (Dec. 2011).
Dontula, R. et al., "MicroRNA 203 Modulates Glioma Cell Migration Via Robo1/ERK/MMP-9 signaling," Genes & Cancer 4(7-8):285-96, SAGE Publications, England (Jul. 2013).
Office Action dated Apr. 16, 2020, in U.S. Appl. No. 16/443,700, Ryu, J-H., et al., filed Jun. 17, 2019, 13 pages.
Watts, J.K., and Corey, D.R., "Silencing disease genes in the laboratory and the clinic," J Pathol 226(2):365-79, John Wiley & Sons, Inc., United States (Jan. 2012).
Cohen, J.E., et al., "MicroRNA Regulation of Homeostatic Synaptic Plasticity," Proceedings of the National Academy of Sciences of the United States of America, 108(28):11650-11655, National Academy of Sciences, United States (Jul. 2011).

(56) References Cited

OTHER PUBLICATIONS

Crooke, S.T., "Antisense Research and Application, "Springer-Verlag, Berlin, Germany, 131:103-140, (1998).
International Search Report for Application No. PCT/KR2018/000948, dated May 1, 2018, 2 pages.
Kalra, J and Khan, A., "Reducing Aβ Load And Tau Phosphorylation: Emerging Perspective For Treating Alzheimer's Disease," European Journal of Pharmacology, 764:571-581, Elsevier Science, Netherlands (Oct. 2015).
Lee, S.T., et al., "Mir-206 Regulates Brain-Derived Neurotropic Factor in Alzheimer Disease Model," Annals of Neurology, 72(2):269-277, Wiley-Liss, United States (Aug. 2012).
Lou, C., et al., "MiR-485-3p and miR-485-5p Suppress Breast Cancer Cell Metastasis By Inhibiting Pgc-1 a Expression," Cell Death & Disease, 7(3):e2159, Nature Publishing Group, England (Mar. 2016).
Scheckel, C., et al., "Regulatory Consequences of Neuronal Elav-Like Protein Binding To Coding and Non-Coding RNAs In Human Brain," Elife, 5: e10421, elife Sciences Publications, England (Feb. 2016).
Wang, W.X., et al., "Patterns of microRNA expression in normal and early Alzheimer's disease human temporal: white matter versus gray matter," Acta Neuroopathol 121 (2):193-205, Springer+ Business Media, Germany (Feb. 2011).

\* cited by examiner

FIG. 2

| miRNA binding location 841, 1621, 1675 of hELAVL2 3' UTR Sequence<br>GenBank: NM 001171197 | 3'  — TGTATGA ——————— <br>                     ||||||| |
|---|---|
| has-miR-485-3p | 5'  GUCAUACACGGCUCUCCUCUCU |
| miRNA binding location 841, 1621, 1675 of hELAVL2 conserved mELAVL2 3' UTR Sequence<br>GenBank: BC058393.1 | 3'  — TGTATGA ——————— <br>                     ||||||| |
| mmu-miR-485-3p | 5'  AGUCAUACACGGCUCUCCUCUC |

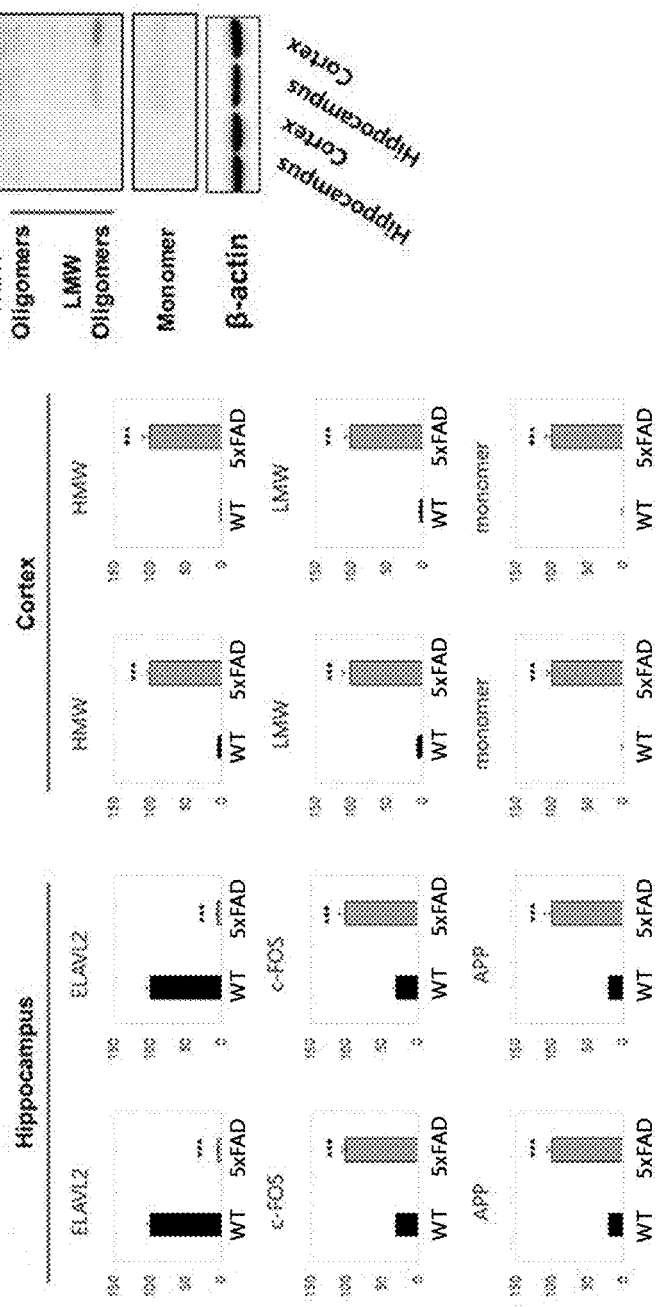
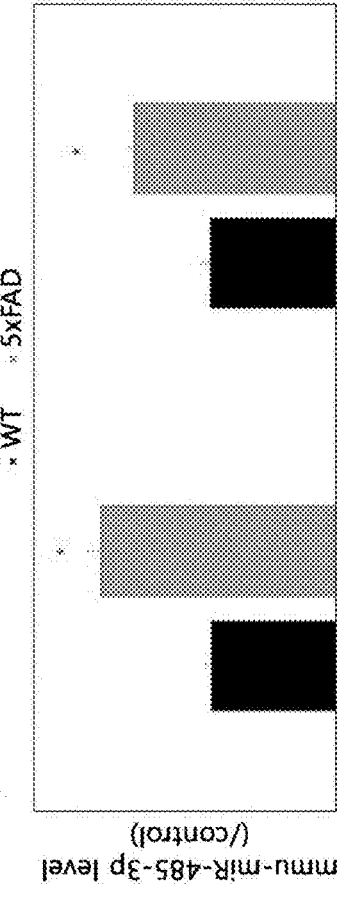
FIG. 3A
FIG. 3B
FIG. 3C

FIG. 6A
FIG. 6B
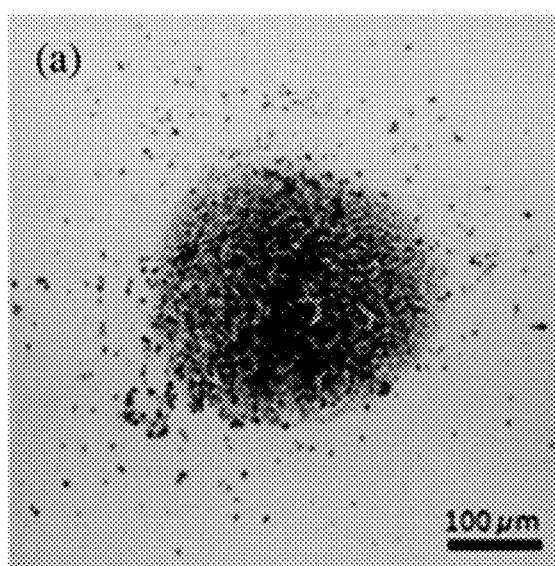
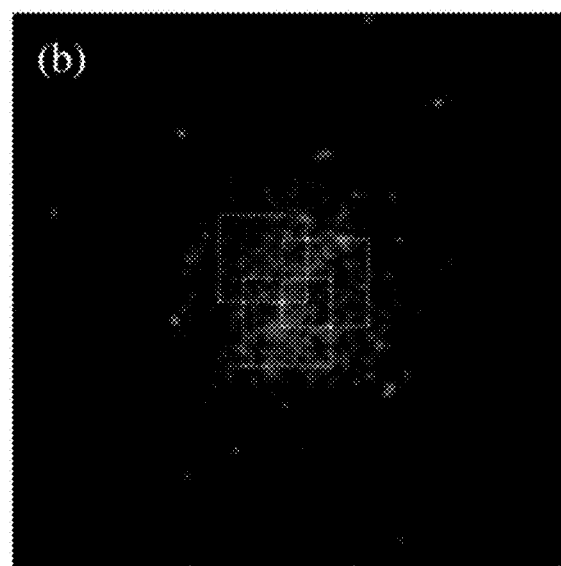

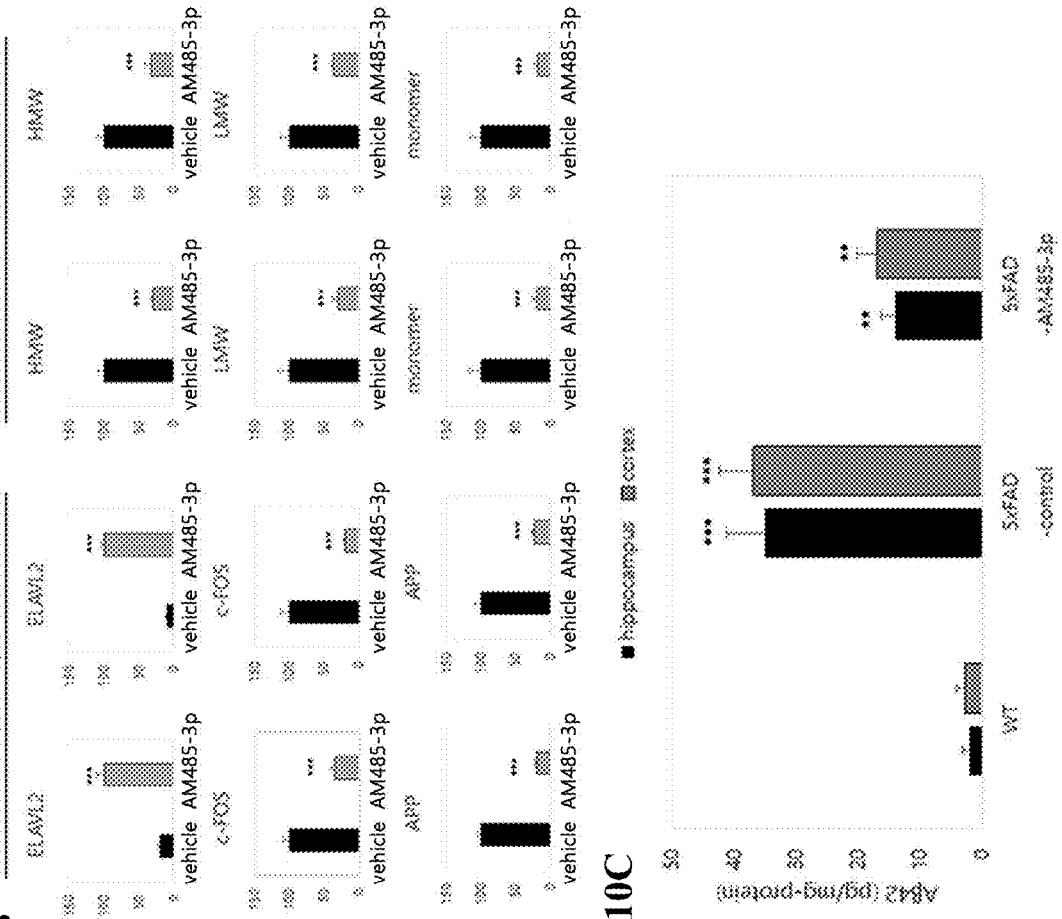
FIG. 10B
FIG. 10C
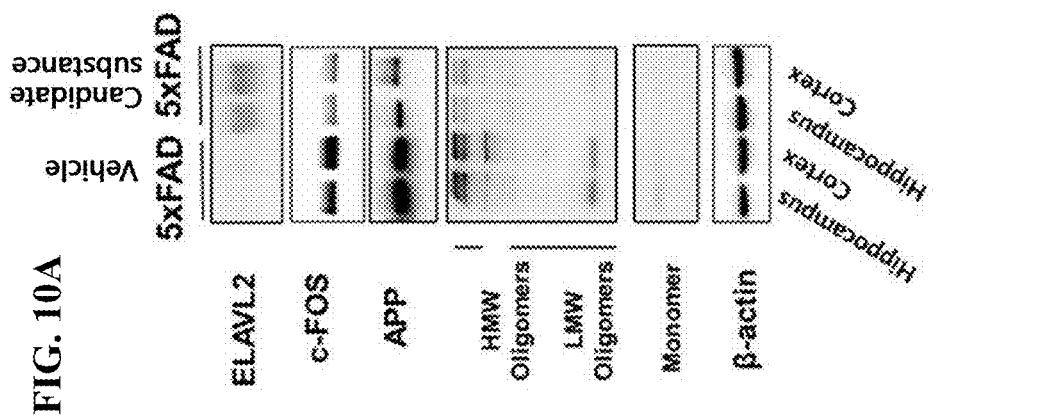
FIG. 10A

SEQUENCE LISTING

```
<160> NUMBER OF SEQ ID NOS: 11

<210> SEQ ID NO 1
<211> LENGTH: 22
<212> TYPE: RNA
<213> ORGANISM: Artificial Sequence
<220> FEATURE:
<223> OTHER INFORMATION: miR-485-3p

<400> SEQUENCE: 1
gucauacacg gcucuccucu cu                                            22

<210> SEQ ID NO 2
<211> LENGTH: 73
<212> TYPE: RNA
<213> ORGANISM: Artificial Sequence
<220> FEATURE:
```

```
<223> OTHER INFORMATION: miR-485-3p

<400> SEQUENCE: 2
acuuggagag aggcuggccg ugaugaauuc gauucaucaa agcgagucau acacggcucu     60
ccucucuuuu agu                                                       73

<210> SEQ ID NO 3
<211> LENGTH: 9
<212> TYPE: RNA
<213> ORGANISM: Artificial Sequence
<220> FEATURE:
<223> OTHER INFORMATION: miR-485-3p

<400> SEQUENCE: 3 guguaugac                                                             9

<210> SEQ ID NO 4
<211> LENGTH: 8
<212> TYPE: RNA
<213> ORGANISM: Artificial Sequence
<220> FEATURE:
<223> OTHER INFORMATION: miR-485-3p

<400> SEQUENCE: 4 uguaugac                                                              8

<210> SEQ ID NO 5
<211> LENGTH: 8
<212> TYPE: RNA
<213> ORGANISM: Artificial Sequence
<220> FEATURE:
<223> OTHER INFORMATION: miR-485-3p

<400> SEQUENCE: 5 guguauga                                                              8

<210> SEQ ID NO 6
<211> LENGTH: 7
<212> TYPE: RNA
<213> ORGANISM: Artificial Sequence
<220> FEATURE:
<223> OTHER INFORMATION: miR-485-3p

<400> SEQUENCE: 6 uguauga                                                               7

<210> SEQ ID NO 7
<211> LENGTH: 22
<212> TYPE: RNA
<213> ORGANISM: Artificial Sequence
<220> FEATURE:
<223> OTHER INFORMATION: miR-485-3p

<400> SEQUENCE: 7
agagaggaga gccguguaug ac                                              22

<210> SEQ ID NO 8
<211> LENGTH: 22
<212> TYPE: RNA
<213> ORGANISM: Artificial Sequence
<220> FEATURE:
<223> OTHER INFORMATION: mmu-miR-485-3p

<400> SEQUENCE: 8
agucauacac ggcucuccuc uc                                              22
```

```
<210> SEQ ID NO 9
<211> LENGTH: 22
<212> TYPE: RNA
<213> ORGANISM: Artificial Sequence
<220> FEATURE:
<223> OTHER INFORMATION: antagomir

<400> SEQUENCE: 9
gagaggagag ccguguauga cu                                              22

<210> SEQ ID NO 10
<211> LENGTH: 17
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (4)..(4)
<223> OTHER INFORMATION: n is a, c, g, or t

<400> SEQUENCE: 10
nnvngtcata cacggct                                                    17

<210> SEQ ID NO 11
<211> LENGTH: 27
<212> TYPE: DNA
<213> ORGANISM: Artificial Sequence
<220> FEATURE:
<223> OTHER INFORMATION: primer

<400> SEQUENCE: 11
ccagtttttt ttttttttta gagagga                                         27
```

METHOD FOR DIAGNOSIS OF ALZHEIMER'S DISEASE USING MICRORNA

REFERENCE TO SEQUENCE LISTING SUBMITTED ELECTRONICALLY VIA EFS-WEB

The content of the electronically submitted sequence listing in ASCII text file (Name: 4366_0130000_SeqListing_ST25.txt; Size: 2,487 bytes; and Date of Creation: Jun. 13, 2019) filed with the application is herein incorporated by reference in its entirety.

TECHNICAL FIELD

The present disclosure relates to a method for diagnosing Alzheimer's disease or a brain disease using a microRNA. More particularly, it relates to a method for diagnosing Alzheimer's disease or a brain disease, which includes a step of measuring the expression level of the microRNA miR-485-3p in a sample. In addition, it relates to a composition and a diagnostic kit for diagnosing Alzheimer's disease or a brain disease using miR-485-3p or amyloid beta 42.

BACKGROUND OF THE DISCLOSURE

The treatment of Alzheimer's disease has recently focused on the observation that Alzheimer's disease may be caused by impaired cholinergic signaling and transmission in the cerebral cortex and hippocampus (Bartus et al., *Science.* 217(4558): 408-14(1982) and Coyle et al., *Science.* 219 (4589): 1184-90(1983)).

Because these regions of the brain are associated with memory and intelligence, functional deficit in these regions may cause loss of memory and intelligence. Although the process of impairment in neuronal signaling is still controversial, senile plaques and neurofibrillary tangles (NFT) are considered as main pathological causes.

In particular, development of senile plaques due to the accumulation of amyloid beta (Aβ) is a notable feature of this disease, and Alzheimer's disease can be confirmed by post-mortem examination (Khachaturian, *Arch. Neurol.* 42(11): 1097-105(1985)).

As a way of treating Alzheimer's disease, a method of increasing the amount of acetylcholine to inhibit the impairment of cholinergic signaling or causing acetylcholine to act more effectively on transmission of neuronal cells has been proposed. Thus, patients with Alzheimer's disease use a variety of compounds for increasing the activity of acetylcholine.

Currently, the most effective way is to rapidly decompose acetylcholine in synapses, thus inhibiting the activity of acetylcholinesterase that prevents neuronal signaling. These inhibitors (e.g., tacrine, donepezil, galantamine and rivastigmine) are approved by the United States Food and Drug Administration (FDA) and are currently available on the market as Alzheimer's disease medications. Despite their effectiveness in preventing further destructive progress of this disease, they are not used to cure the disease.

Some compounds are aimed to improve the neuronal state and maintain aged cells in good function. For example, some drugs such as NGF or estrogen act as neuroprotecting agents to delay neurodegeneration, and other drugs such as antioxidants decrease cell damage caused by oxidation of cells resulting from normal aging.

Alzheimer's disease becomes serious as amyloid beta peptide is accumulated in the neuritic space. It is thought that the progress of Alzheimer's disease can be delayed by reducing the accumulation of amyloid beta. In addition, amyloid precursor protein (APP) is considered to play a role in cells in combination with proteinases such as α-, β- and γ-secretases. However, because the process of amyloid beta formation has not been fully elucidated scientifically, it is not possible to control the formation of amyloid beta.

It is not certain how the accumulation of amyloid beta acts on neuronal signaling. Abnormally cleaved APP induces amyloid beta generation, and plaque formation is induced by the accumulation of amyloid beta in neuritic space. Thus, various factors involved in this cleavage reaction (e.g., Inflammation reaction, etc.) increase the phosphorylation of tau protein, and also increase the accumulation of paired helical filaments (PHF) in combination with NFT, resulting in damage to the nerve. All these factors induce dysfunction of the nerve and, ultimately, accelerate the progress of Alzheimer's disease to dementia.

Although the development of therapeutic methods to reduce the effect of Alzheimer's disease is carried out actively, temporary improvement of symptoms is the current strategy. In conclusion, the current treatment of Alzheimer's disease is just focused on improvement of symptoms instead of slowing or reversing the progress of the disease. Despite the biological knowledge about the disease, clinical application is still not successful.

In this regard, U.S. Pat. No. 5,532,219 discloses a composition for treating Alzheimer's disease containing 4,4'-diaminodiphenylsulfone, etc., U.S. Pat. No. 5,506,097 discloses a composition for treating Alzheimer's disease containing para-amidinophenylmethanesulfonyl fluoride or ebelactone A, and U.S. Pat. No. 6,136,861 discloses a composition for treating Alzheimer's disease containing bicyclo[2.2.1]heptane.

ELAVL2, or ELAVL-like neuron-specific RNA binding protein 2, is a type of nELAVL2. nELAVL2 is an RNA-binding protein expressed specifically in the brain and is known to be associated with neurodegenerative diseases. As a result of conducting high-throughput RNA sequencing using brain tissue after post-mortem of patients with Alzheimer's disease, it was found out that ELAVL2 was expressed with low levels.

Alzheimer's disease is the most common form of dementia. 75% of patients with dementia have Alzheimer's disease. In most cases, Alzheimer's disease begins in people over 65 years of age, although it can occur earlier in rare cases. In the United States, about 3% of the population aged 65-74 years, about 19% of the population aged 75-84 years, and 50% of the population aged over 85 years suffer from this disease. In Korea, according to a recently reported study on a rural region, about 21% of the population aged over 60 years in the rural region showed dementia, and 63% of them had Alzheimer's dementia. In 2006, 266,000 people around the world had the disease. It is expected that the disease will occur in one out of every 85 people in 2050.

There is no cure for Alzheimer's dementia and the only method of management is diagnosis followed by prescription of relievers. In addition, no early diagnostic system is available. Although a variety of diagnostic methods exist, they have many disadvantages. The questionnaire may have errors due to difference in perception, the structural brain imaging is expensive, and the nuclear medical brain imaging has the disadvantage of using radioactive isotopes and being expensive. The tau protein measurement through the analysis of the cerebrospinal fluid is an invasive method and has a risk associated with the extraction of the cerebrospinal fluid.

Thus, the inventors of the present disclosure have made efforts to select a marker that can diagnose brain diseases such as Alzheimer's disease and develop a more accurate diagnostic method. As a result, they have confirmed the increased expression level of miR-485-3p extracted from blood and have completed the present disclosure.

The information described in the Background section is only to enhance the understanding of the background of the present disclosure, and the information forming the prior art already known to those having ordinary skill in the art to which the present disclosure belongs may not be included.

SUMMARY OF THE DISCLOSURE

The present disclosure is directed to providing a method for diagnosing Alzheimer's disease or a brain disease and a method for providing information for the early diagnosis thereof by measuring the expression level of miR-485-3p.

The present disclosure is also directed to providing a composition and a diagnostic kit for diagnosing Alzheimer's disease or a brain disease.

The present disclosure is also directed to providing a use of a composition for measuring the expression level of miR-485-3p or the concentration of amyloid beta 42 in the diagnosis of Alzheimer's disease or a brain disease.

In order to achieve the above-described objects, the present disclosure provides a method for diagnosing Alzheimer's disease or a brain disease and a method for providing information for the diagnosis thereof, which include a step of measuring the expression level of miR-485-3p in a sample.

The present disclosure also provides a composition or a diagnostic kit for diagnosing a brain disease such as Alzheimer's disease, etc., wherein the kit is used to measure the expression level of miR-485-3p or the concentration of amyloid beta 42.

The present disclosure also provides a use of a composition for measuring the expression level of miR-485-3p or the concentration of amyloid beta 42 in the diagnosis of Alzheimer's disease or a brain disease.

BRIEF DESCRIPTION OF DRAWINGS

FIG. 2 shows the seed sequence of 3'-untranslated region (UTR) mRNA and miR-485-3p of 5xFAD.

FIGS. 3A-3C show a graph comparing the expression of miR-485-3p in the hippocampus and cortex (FIG. 3A) and a result of comparing the expression of ELAVL2 and related proteins in the hippocampus and cerebral cortex of 5xFAD (FIGS. 3B and 3C).

FIGS. 6A-6B show results of quantifying saliva-derived Aβ using a magnetic particle collection device.

FIGS. 10A-10C show comparative quantitative analysis results of ELAVL2 and related proteins and Aβ 42 in 5xFAD intranasally treated with AM485-3p.

Figure 1A:
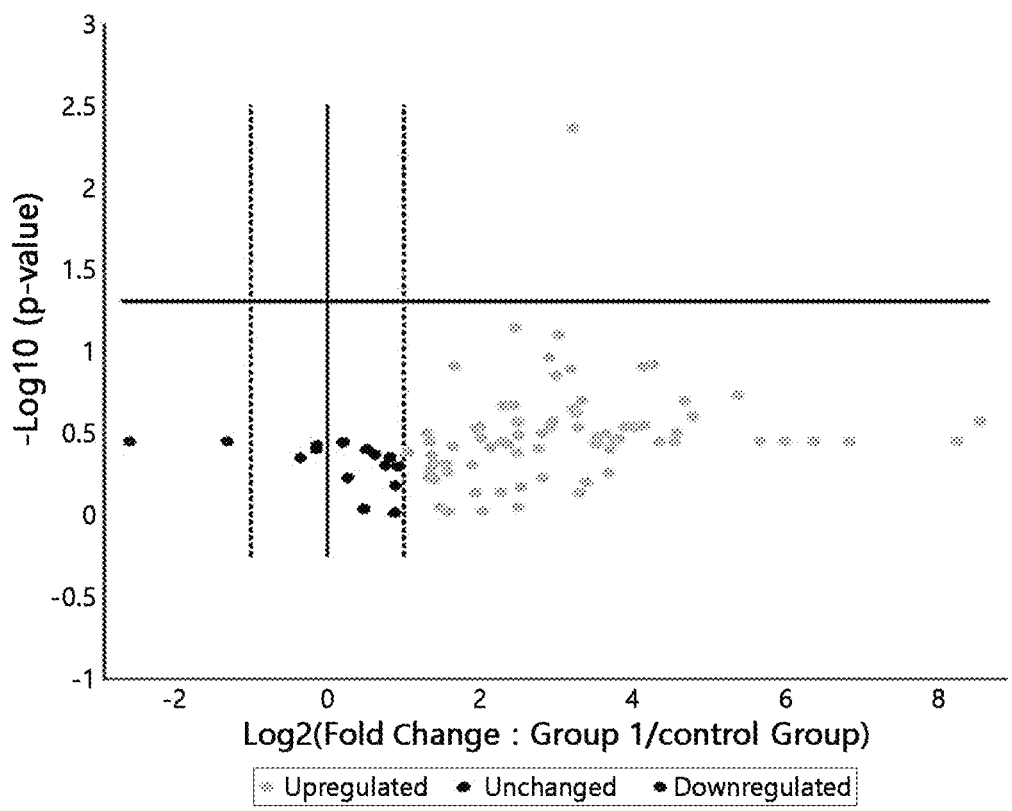
FIGS. 1A-1B show a miRNA expression pattern analysis result (volcano plot) for a patient group as compared to a normal group (FIG. 1A), and a graph comparing the expression of miR-485-3p in a patient group compared to a normal group (FIG. 1B).

Unless defined otherwise, all technical and scientific terms used herein have the same meaning as commonly understood by the skilled experts in the art to which the present disclosure belongs. In general, the nomenclature used herein is known well and commonly used in the art.

In a specific example of the present disclosure, the expression of miR-485-3p was found to increase significantly in the blood obtained from a patient diagnosed with Alzheimer's dementia by a physician.

Thus, in an aspect, the present disclosure relates to a method for providing information for the diagnosis of Alzheimer's disease or a brain disease, which includes a step of measuring the expression level of miR-485-3p from a sample.

In another aspect, the present disclosure relates to a method for diagnosing Alzheimer's disease or a brain disease, which includes a step of measuring the expression level of miR-485-3p in a sample.

The present disclosure may include a step of extracting the microRNA miR-485-3p from the sample. The sample may be blood or plasma, although not being limited thereto.

In the example of the present disclosure, about 3 mL of blood was taken from a patient diagnosed with Alzheimer's dementia by a physician into a blood tube (Becton Dickinson, Germany) to which sodium citrate (3.2% w/v) was added. The blood was centrifuged at 3,500 rpm for 10 minutes to separate plasma, and then stored at −80° C. until RNA extraction. miRNA was extracted using the miRNeasy Serum/Plasma kit (Qiagen, USA) according to the manufacturer's recommendations. The miRNA extraction is performed in the following order. After lysing the blood plasma or serum sample with the QIAzol lysis reagent and then adding chloroform, the lysate is separated into an aqueous phase and organic phase by centrifugation. RNA partitions to the upper aqueous phase, while DNA partitions to the intermediate layer and proteins to the intermediate layer or the lower organic phase. The upper aqueous phase is extracted and ethanol is added to provide a condition appropriate for binding with RNA molecules of at least about 18 nucleotides. The sample is applied to the RNeasy MinElute spin column such that all RNA is bound to a membrane and phenol and other contaminants are washed off efficiently. High-quality RNA is eluted in a small amount of water without RNase. Because serum and plasma mainly contain small RNAs, it is not necessary to additionally purify small and large RNA fractions.

The present disclosure includes a step of measuring the expression level of the microRNA miR-485-3p.

In the present disclosure, the expression level of miR-485-3p may be measured by a method selected from a group consisting of real-time PCR, quantitative PCR, primer extension, nucleic acid chip analysis, sequencing, aptamer-based assay and gel electrophoresis, although not being limited thereto.

In an example of the present disclosure, the concentration and purity of the extracted RNA were analyzed using Bioanalyzer2100 (Agilent, USA). The extracted RNA was screened using the miRNA array containing 84 different miRNAs known to be associated with human neurological development and the progress of neurological disease.

The quantitative PCR assay method can be summarized as follows. A mature miRNA is generally a 22-nucleotide, non-coding RNA and is responsible for post-transcriptional regulation. Polyadenylation of mature miRNA was induced by poly(A) polymerase, and cDNA was synthesized using oligo-dT primers. The oligo-dT primer enables the amplification of the mature miRNA during the real-time PCR process because it has a 3' degenerate anchor and a universal tag sequence at the 5' end. The mature miRNA was quantified during the real-time PCR process using the miScript SYBR Green PCR kit (Qiagen).

In the present disclosure, Alzheimer's disease or a brain disease may be diagnosed if the expression level of miR-485-3p is 5 times or larger, more specifically 9 times or larger, as compared to a normal group. Those who were aged between 59 and 64 years and had no history of Alzheimer's disease or a brain disease were selected as the control group.

In the present disclosure, the brain disease may be any one selected from a group consisting of autism spectrum disorder, mental retardation, amyotrophic lateral sclerosis, seizure, stroke, Parkinson's disease and spinal cord injury, although not being limited thereto.

In the method for providing information and the diagnostic method according to the present disclosure, when diagnosing Alzheimer's disease and/or a brain disease of a subject or determining the prognosis thereof using the expression level of the marker, non-marker clinical information of the subject showing seizure can be further used. The non-marker clinical information of the test subject includes the age, sex, body weight, diet, body mass, underlying diseases, brain waves, type of seizure, brain Mill, brain CT, cerebral spinal fluid test result, blood test result and saliva test result of the subject, although not being limited thereto.

In the present disclosure, the method for providing information for diagnosis of Alzheimer's disease or a brain disease may further include a step of measuring the concentration of amyloid beta 42 (Aβ42) from a sample.

The sample may be saliva or blood, but is not limited thereto. The use of saliva as the sample minimizes the risk for the patient and enables fast and accurate diagnosis.

The concentration of amyloid beta 42 may be measured using an antigen-antibody reaction or a nucleic acid aptamer, although not being limited thereto. The antigen-antibody reaction may be one well-known in the art, including ELISA (enzyme-linked immunosorbent assay). Specifically, when the concentration of amyloid beta 42 is measured from saliva, the measurement may be performed by referring to Korean Patent Publication No. 10-2014-0025978 or Korean Patent Publication No. 10-2013-0140528, although not being limited thereto.

In the present disclosure, the term 'aptamer' refers to a nucleic acid having a specific binding affinity for a target molecule. In the present disclosure, the target molecule may be specifically amyloid beta 42.

The specific binding affinity of the aptamer to the target means that the aptamer binds to the target with a higher degree of affinity than to other components in the sample. The aptamer refers to one or more set of such molecules. Different aptamers may have the same or different number of nucleotides. The aptamer can be DNA, RNA or a chemically modified nucleic acid. It may contain a single-stranded or double-stranded region and may include a highly ordered structure. The aptamer may also be photoaptamer as long as a photoreactive or chemically reactive functional group is included in the aptamer to be covalently bonded to its corresponding target. In the method described in the present disclosure, two or more aptamers that bind specifically to the same target molecule may be used.

The aptamer can be identified using any known method, including SELEX. Once confirmed, the aptamer can be prepared or synthesized according to any known method, including chemical synthesis methods and enzymatic synthesis methods.

The terms "SELEX" and "SELEX process" are used interchangeably herein to refer generally to a combination of (1) the selection of an aptamer that interacts with a target molecule in a desirable manner, for example, by binding with high affinity to a protein, and (2) the amplification of the selected nucleic acid. The SELEX process can be used to identify an aptamer having high affinity for a specific target or biomarker. SELEX generally includes preparing a candidate mixture of nucleic acids, binding of the candidate mixture to a desired target molecule to form an affinity complex, separating the affinity complex from the unbound candidate nucleic acids, separating and isolating the nucleic acids from affinity complex, purifying the nucleic acids, and amplifying a specific aptamer sequence. The process may include multiple rounds to further refine the affinity of the selected aptamer. The process can include an amplification step at one or more points in the process (see, e.g., U.S. Pat. No. 5,475,096: Nucleic acid ligands). The SELEX process can be used to generate an aptamer that binds covalently to its target as well as an aptamer that binds non-covalently to its target (see, e.g., U.S. Pat. No. 5,705,337: Systematic evolution of nucleic acid ligands by exponential enrichment: Chemi-SELEX). The SELEX process can be used to identify a high-affinity aptamer containing a modified nucleotide that confers improved characteristics on the aptamer, such as, for example, improved in vivo stability or improved delivery characteristics. Examples of such modification include chemical substitution at the ribose and/or phosphate and/or base position. The aptamer identified in the SELEX process is described in U.S. Pat. No. 5,660,985 ("High affinity nucleic acid ligands containing modified nucleotides"), which describes an oligonucleotide containing a nucleotide derivative chemically modified at the 5'- and 2'-positions of pyrimidine. U.S. Pat. No. 5,580,737 describes a highly specific aptamer containing one or more nucleotide modified with 2'-amino (2'-$NH_2$), 2'-fluoro (2'-F) and/or 2'-O-methyl (2'-OMe). See also US Patent Application Publication No. 2009/0098549 (SELEX and PHOTOSELEX), which describes nucleic acid libraries having expanded physical and chemical properties and their in SELEX and photo-SELEX. SELEX can also be used to identify aptamers that have desirable off-rate characteristics. See US Patent Application No. 2009/0004667 (Method for generating aptamers with improved off-rates), which describes an improved SELEX method for generating aptamer capable of binding to a target molecule.

The aptamer is immobilized on a solid support before being contacted with the sample. However, under certain circumstances, the immobilization of the aptamer prior to contact with the sample may not provide an optimal assay. For example, pre-immobilization of the aptamer possibly can lead to inefficient mixing of the target molecule on the solid support surface and the aptamer due to the long reaction time. Thus, a long incubation period is required for efficient binding of the aptamer to its target molecule. In addition, if a photoaptamer is used in the assay and if it depends on the material used as the solid support, the solid support may tend to scatter or absorb the light used to form a covalent bond between the photoaptamer and its target molecule. Furthermore, depending on the method used, the surface of the solid support may be exposed to a labeling reagent and can be affected by it. Therefore, the detection of the target molecule binding to its aptamer is susceptible to imprecision. Finally, the immobilization of the aptamer on the solid support generally includes an aptamer preparation (i.e., immobilization) step prior to exposure of the aptamer to the sample, and this preparation step can influence the activity or functionality of the aptamer.

The aptamer may be constructed to facilitate separation of the assay components from an aptamer-biomarker complex (or a photoaptamer-biomarker covalent complex) and permit isolation of the aptamer for detection and/or quantification. In one embodiment, the construct may contain a cleavable or releasable component within the aptamer sequence. In another embodiment, additional functionality such as a labeled or detectable component, a spacer component or a specific binding tag or immobilization component can be introduced into the aptamer. For example, the aptamer can include a tag connected to the aptamer via a cleavable moiety, a label, a spacer component separating the label, and the cleavable moiety.

The nucleic acid aptamer may be any one selected from a group consisting of DNA, RNA, an antagomir (anti-miR), an antisense molecule, a small interfering RNA (siRNA) molecule, a small hairpin RNA (shRNA) molecule, a 2'-O-modified oligonucleotide, a phosphorothioate-backbone deoxyribonucleotide, a phosphorothioate-backbone ribonucleotide, a decoy oligonucleotide, a PNA (peptide nucleic acid) oligonucleotide, or an LNA (locked nucleic acid) oligonucleotide, although not being limited thereto.

In an example of the present disclosure, a multi-nucleic acid with the structural features that, upon binding to amyloid beta 42, fluorescence is emitted as a quencher is detached at the same time was synthesized by using a sequence binding specifically to amyloid beta 42 and a sequence self-coupled within the nucleic acid. Because the size of the multi-nucleic acid is smaller than an antibody, its specificity and selectivity are excellent. Also, because sampling and large-scale analysis are possible within one hour, it can provide a diagnostic method with high diagnostic ease.

In the present disclosure, normality may be diagnosed if the concentration of amyloid beta 42 is equal to or higher than 0 and below 500 pg/mL, mild cognitive impairment (MCI) may be diagnosed if is equal to or higher than 500 pg/mL and below 1 ng/mL, and severe cognitive impairment may be diagnosed if is equal to or higher than 1 ng/mL.

In an example of the present disclosure, when the amyloid beta 42 level of over 100 dementia patients was normalized through a previous study, mild cognitive impairment and moderate dementia could be distinguished successfully (90% or higher match with diagnosis by clinicians).

In an example of the present disclosure, it was confirmed that the increase pattern of miR-485-3p significantly affects the expression level of APP, which is known as an amyloid beta precursor.

In another aspect, the present disclosure relates to a composition for diagnosing Alzheimer's disease or a brain disease, which contains a primer capable of amplifying miR-485-3p or a probe capable of hybridizing with miR-485-3p.

In the present disclosure, the primer is constructed so as to have complementarity roughly to each strand of miR-485-3p to be amplified, and contains a suitable G or C nucleotide. This means that the primer has sufficient complementarity to the corresponding nucleic acid strand to be hybridized under the conditions for the polymerization reaction. In the present disclosure, the primer is used for an amplification process. The amplification process is a continuous enzymatic reaction in which the number of a target locus increases exponentially over the course of the reaction, such as PCR. Typically, one primer (antisense primer) has homology to the negative strand of a locus (−), and the other primer (sense primer) has homology to the positive (+) strand. When the primer is annealed to a denatured nucleic acid, the chain is extended by enzymes and reaction products, such as DNA polymerase I (Klenow) and nucleotides. As a result, + and − strands containing the target locus sequence are newly synthesized. The newly synthesized target locus is also used as a template, such that the synthesis of the target locus sequence proceeds exponentially as the cycle of denaturation, primer annealing and chain extension is repeated. The products of the continuous reaction are individual double-stranded nucleic acids having terminals corresponding to the terminals of the specific primers used in the reaction.

Specifically, the amplification reaction may be PCR, which is commonly used in the art. However, alternative methods such as real-time PCR or linear amplification using an isothermal enzyme may also be used. The multiplex amplification reaction may also be used.

In the present disclosure, the probe may be labeled to be detectable. For example, it may be labeled with a radioisotope, a fluorescent compound, a bioluminescent compound, a chemiluminescent compound, a metal chelator or an enzyme. The appropriate labeling of the probe is a well-known technique in the art and can be carried out by a method commonly used in the art. The probe may be a probe specifically binding to a known nucleic acid biomarker for diagnose of diseases. Through binding to the probe, the presence of a particular biomarker or a fragment thereof can be detected and a disease may be diagnosed based thereon.

In the present disclosure, the sequence of miR-485-3p may be derived from a mammal, for example, human, mouse or rat.

In an exemplary embodiment of the present disclosure, the sequence of miR-485-3p is derived from human, and includes not only a mature sequence (5'GUCAUACACGG-CUCUCCUCUCU 3' (SEQ ID NO 1)) but also a precursor sequence (5'-ACUUG-GAGAGAGGCUGGCCGUGAUGAAUUCGAUUCAU-CAAAGCGAGUCAUAC ACGGCUCUCCUCUC-UUUUAGU-3' (SEQ ID NO 2)).

Therefore, in the present disclosure, the primer or the probe may contain a sequence complementary to the base sequence of SEQ ID NO 1 or SEQ ID NO 2 or a part thereof, although not being limited thereto.

In the present disclosure, the primer may be one represented by SEQ ID NOS 10-11, although not being limited thereto.

```
                                            (SEQ ID NO 10)
    Forward 5'-NNVNgtcatacacggct-3'.

(SEQ ID NO 11)
    Reverse 5'-ccagttttttttttttttagagagga-3'.
```

In the present disclosure, the SEQ ID NO 10 may contain the 1st through 19th base sequences of SEQ ID NO 1 from the 5' end, and N may be g or c, and V may be a or t. The 1st through 19th base sequences and NNVN may be adjusted according to the length of the whole primer.

The SEQ ID NO 11 may contain base sequences complementary to the 14th through 22nd base sequences of SEQ ID NO 1 from the 5' end, may contain 15 t's in a row, and may be attached with universal gacctgg. The sequences complementary to the 14th through 22nd complementary sequences and the gacctgg may be adjusted according to the length of the whole primer.

In the present disclosure, the composition for diagnosing Alzheimer's disease or a brain disease may further contain an antibody or a nucleic acid aptamer or specifically binding to amyloid beta 42. The antibody or nucleic acid aptamer is for detecting amyloid beta 42, and may be used in any form for the detection of amyloid beta 42 from the sample.

In another aspect, the present disclosure relates to a use of a composition containing a primer capable of amplifying miR-485-3p or a probe capable of hybridizing with miR-485-3p in diagnosis of Alzheimer's disease or a brain disease.

In the present disclosure, the composition may further contain an antibody or a nucleic acid aptamer which specifically binds to amyloid beta 42.

In another aspect, the present disclosure relates to a kit for diagnosing Alzheimer's disease or a brain disease, which contains the composition for diagnosing Alzheimer's disease or a brain disease.

The diagnostic kit of the present disclosure may be used in the diagnosis of Alzheimer's disease and/or several brain diseases. Most specifically, it may be used in the diagnosis of Alzheimer's disease.

The kit of the present disclosure may further contain other components in addition to the aforementioned components. For example, if the kit of the present disclosure is applied to a PCR amplification process, it may contain, optionally, a reagent required for PCR amplification such as a buffer, a DNA polymerase, a DNA polymerase cofactor and dNTP, although not being limited thereto. The kit of the present disclosure may be prepared into a number of separate packages or compartments containing the above reagent component.

In addition, the kit according to the present disclosure may be a microarray, specifically a gene amplification kit. If the kit is a microarray, a probe is immobilized on the solid surface of the microarray. If the kit of the present disclosure is a gene amplification kit, it contains a primer. The probe or primer specifically recognizes the miR-485-3p according to the present disclosure and has a sequence complementary to its sequence. The term 'complementary' used herein refers to having complementarity enough for selective hybridization to the nucleotide sequence under certain hybridization or annealing conditions. The probe or primer of the present disclosure may be fully complementary, or may have one or more mismatch base sequence if selective hybridization to the nucleotide sequence is possible. The nucleotide sequence of the miRNA of the present disclosure to be consulted when constructing the primer or probe may be searched from miRBase, and the primer or probe may be designed based on the sequence.

The composition according to the present disclosure, which contains a substance capable of inhibiting the activity miR-485-3p and a pharmaceutically acceptable carrier, may be provided as a pharmaceutical composition for preventing or treating Alzheimer's disease or a brain disease.

The present disclosure provides a pharmaceutical composition for treating or preventing Alzheimer's disease, which contains a substance capable of inhibiting the activity miR-485-3p and a pharmaceutically acceptable carrier, based on the finding that the decreased expression of ELAVL2 by miR-485-3p is associated with Alzheimer's disease.

The "miR" mainly refers to a non-coding RNA consisting of 21-23 deoxyribonucleotides, which is known to be involved in post-transcriptional regulation of gene expression by suppressing the translation of target RNA or promoting degradation thereof.

In addition, the mature sequence of the miRNA can be obtained from the miRNA database (http://www.mirbase-.org). In the miRNA database as of Aug. 13, 2012 (19th edition, miRBase), 25,141 mature miRNAs derived from 193 species are listed.

In the present disclosure, the miR-485-3p is expressed in the brain, particularly in the hippocampus and the cortex, and it binds to the 3'-untranslated region of ELAVL2 mRNA encoding the ELAVL2 protein, thereby inhibiting its expression and decreasing the concentration of the ELAVL2 protein in the brain.

In the present disclosure, the inhibition of the activity of miR-485-3p means the inhibition of or interference with the action or function of miR-485-3p in cells. Typically, it includes direct inhibition of binding of miR-485-3p to a target, e.g., a mRNA molecule encoding the ELAVL2 protein, direct inhibition of the function of miR-485-3p using a small molecule inhibitor, an antibody or an antibody fragment, or indirect regulation using an inhibitor or a small interfering RNA (siRNA) molecule.

Furthermore, the interference with or inhibition of the activity of miR-485-3p includes inhibiting the activity of the precursor sequence (SEQ ID NO 2) or the mature sequence (SEQ ID NO 1) directly or indirectly. In addition, the inhibition of the activity of miR-485-3p includes lowering the concentration thereof in cells by inhibiting the transcription of miR-485-3p.

The substance capable of inhibiting the activity of miR-485-3p includes any substance capable of inhibiting its expression and/or activity. For example, such substance may include a compound (a small molecule or a polymer), an antagomir, an antisense molecule, a small hairpin RNA (shRNA) molecule, a small interfering RNA (siRNA) molecule, a seed-targeting LNA (locked nucleic acid) oligonucleotide, a decoy oligonucleotide, an aptamer, a ribozyme, or an antibody that recognizes a DNA:RNA hybrid.

The antisense oligonucleotide includes a nucleic acid-based molecule having a sequence complementary to the seed sequence of the miRNA completely or partially and thus capable of forming a duplex with miRNA. Thus, the antisense oligonucleotide may be referred to as a complementary nucleic acid-based inhibitor.

In addition, the antisense oligonucleotide includes a variety of molecules, for example, a ribonucleic acid (RNA), a deoxyribonucleic acid (DNA), an antagomir, a 2'-O-modified oligonucleotide, a phosphorothioate-backbone deoxyribonucleotide, a phosphorothioate-backbone ribonucleotide, a PNA (peptide nucleic acid) oligonucleotide or an LNA (locked nucleic acid) oligonucleotide. Specifically, it may be a ribonucleic acid.

The ribonucleic acid includes a double-stranded small hairpin RNA (shRNA) molecule, a small interfering RNA (siRNA) molecule and a ribozyme.

The LNA is has a locked conformation due to further modification between the 2' and 4' carbon of the ribose moiety of the oligonucleotide and, thus, ensures thermal stability.

The PNA (peptide nucleic acid) contains a peptide-based backbone instead of a sugar-phosphate backbone. The 2'-O-modified oligonucleotide is specifically a 2'-O-alkyl oligonucleotide, more specifically a 2'-O—$C_{1-3}$ alkyl oligonucleotide, and most specifically a 2'-O-methyl oligonucleotide.

The antisense oligonucleotide includes an antisense oligonucleotide in a narrow sense, an antagomir and an inhibitory RNA molecule.

The antagomir is a chemically modified single-stranded oligonucleotide and is used to silence an endogenous microRNA. The antagomir contains a sequence that is not complementary at the Argonaute 2 (Ago2) cleavage site, or inhibits cleavage of Ago2 such that the base is modified with, for example, a 2-'methoxy group, a 3'-cholesterol group or a phosphorothioate. There is a complementary sequence to the target sequence.

In the present disclosure, the antagomir has a sequence which is at least partially or completely complementary to miR-485-3p. In an exemplary embodiment of the present disclosure, the antagomir includes one or more modification (e.g., 2'-O-methyl-sugar modification or 3'-cholesterol modification). In another embodiment, the antagomir contains one or more phosphorothioate linkage and has a phosphorothioate backbone at least in part.

In the present disclosure, the appropriate length of the antagomir for inhibiting the expression of miR-485-3p is 7-50 nucleotides, particularly 10-40 nucleotides, more particularly 15-30 nucleotides, particularly 15-25 nucleotides, more particularly 16-19 nucleotides, although not being limited thereto.

The term 'complementary' as used the present disclosure means that the antisense oligonucleotide is sufficiently complementary to a target of miR-485-3p under predetermined hybridization conditions or annealing conditions, specifically under physiological conditions, such that it can selectively hybridize to the target, and encompasses both partially or substantially complementary and completely (perfectly) complementary. Specifically, it means being completely complementary. Substantially complementary means that, although not completely complementary, it has complementarity sufficient to bind to the target sequence and exert an effect according to the present disclosure, i.e., interference with the activity of miR-485-3p.

The 'nucleic acid' includes an oligonucleotide, DNA, RNA, a polynucleotide, and analogs derivatives thereof. For example, a peptide nucleic acid (PNA) or a mixture thereof is included. In addition, the nucleic acid may be single- or double-stranded and can encode molecules including mRNA, microRNA, siRNA, polypeptides, etc.

In an exemplary embodiment of the present disclosure, the substance capable of inhibiting the activity of miR-485-3p is an antisense oligonucleotide which is capable of complementarily binding to all or a portion of the progenitor and/or mature sequence of miR-485-3p, particularly the seed sequence, thereby inhibiting its activity. The inhibition of the activity is to inhibit the transcription of miR-485-3p and/or binding to the target mRNA of miR-485-3p. The antisense oligonucleotide according to the present disclosure may or may not include one or more modification in nucleotides constituting the antisense oligonucleotide or the backbone connecting the nucleotides. That is to say, at least one nucleotide constituting the antisense oligonucleotide may contain LNA, the sugar of at least one nucleotide constituting the same may be 2'-O-methylated or methoxylated, or one or more phosphothioate may be contained in the backbone.

In an exemplary embodiment of the present disclosure, the antisense oligonucleotide or the nucleic acid molecule contains a sequence complementary to all or a portion of the seed sequence of miR-485-3p. The seed sequence conserved in a variety of species is a sequence which is very important in recognition of the target molecule of miRNA (Krenz, M. et al., *J. Am. Coll. Cardiol.* 44: 2390-2397(2004); H. Kiriazis, et al., *Annu. Rev. Physiol.* 62: 321(2000)). Because miRNA binds to its target via the sequence seed, the translation, etc. of the target mRNA may be inhibited effectively by inhibiting the interaction between the seed sequence and the target.

In an exemplary embodiment of the present disclosure, the antisense oligonucleotide of the present disclosure may contain a sequence which is complementary completely or partially to the 1st or 2nd through the 7th or 8th nucleotide sequence of the nucleotide sequence of SEQ ID NO 1. For example, the antisense oligonucleotide of the present disclosure may be 5'-GUGUAUGAC-3' (SEQ ID NO 3), 5'-UGUAUGAC-3' (SEQ ID NO 4), 5'-GUGUAUGA-3' (SEQ ID NO 5), 5'-UGUAUGA-3' (SEQ ID NO 6) or 5'-AGAGAGGAGAGCCGUGUAUGAC-3' (SEQ ID NO 7), and one or more of each nucleotide constituting the oligonucleotide may be 2'-O-methylated or methoxylated, ethyl, one or more of each nucleotide may be LNA, one or more chemical bond constituting the backbone may be phosphothioate, or there may be no modification.

The present disclosure is based on the finding that the excessive inhibition of ELAVL2 expression by miR-485-3p is involved in the development of Alzheimer's disease and various brain diseases.

It is known that the decreased expression level of ELAVL2 is associated with the onset of Alzheimer's disease, autism spectrum disorder, mental retardation and amyotrophic lateral sclerosis. Especially, it is known that the level of the ELAVL2 protein is decreased by substances inducing excitotoxicity such as kainic acid, NMDA, quisulate, AMPA, glutamate, etc., resulting in neuronal cell death and disturbance of brain function, causing a number of brain diseases such as seizure, stroke, Parkinson's disease, spinal cord injury, etc. (Kaminska, B. et al., *Acta Biochim Pol.* 44: 781-789).

Therefore, the recovery of the ELAVL2 protein through the inhibition of the activity of miR-485-3p according to the present disclosure can be used in the treatment of various brain diseases such as Alzheimer's disease, autism spectrum disorder, mental retardation, amyotrophic lateral sclerosis, seizure, stroke, Parkinson's disease, spinal cord injury, etc.

In an exemplary embodiment of the present disclosure, the pharmaceutical composition containing a substance capable of inhibiting the activity of miR-485-3p may be used in the treatment of a brain disease. The brain disease includes Alzheimer's disease, autism spectrum disorder, mental retardation, amyotrophic lateral sclerosis, seizure, stroke, Parkinson's disease and spinal cord injury, but is not limited thereto.

The term 'improvement', 'treatment', 'alleviation' or 'improvement' as used in the present disclosure means any action to change favorably or improve the symptoms of related diseases by administering the composition. Those of ordinary skill in the art to which the present disclosure belongs will know the exact criteria of diseases by referring to the data presented, for example, by the Korean Academy of Medical Sciences, and will be able to judge the degree of improvement, progress and treatment.

The term "prevention" as used in the present disclosure means any action to inhibit or delay the onset of related diseases. It will be apparent to those skilled in the art that the related diseases can be prevented if the pharmaceutical composition according to the present disclosure is administered when or before early symptoms appear.

In the present disclosure, the pharmaceutical composition may further contain, in addition to the substance capable of inhibiting the activity of miR-485-3p, one or more active ingredient exhibiting the same, similar or synergistic function for the treatment of related diseases or a compound which maintains/increases the solubility and/or absorbency of the substance capable of inhibiting the activity of miR-485-3p or the active ingredient. And, optionally, it may further contain an immunomodulator and/or a chemotherapeutic agent.

The pharmaceutical composition may further contain one or more pharmaceutically acceptable diluent, carrier and/or adjuvant in addition to the above-mentioned active ingredient. As the pharmaceutically acceptable carrier, saline, sterile water, Ringer's solution, buffered saline, dextrose solution, maltodextrin solution, glycerol, ethanol, liposome, and a mixture of one or more of these components may be used. If necessary, other common additives such as an antioxidant, a buffer, a bacteriostatic agent, etc. may be added.

In addition, it can be formulated into an injectable formulation such as an aqueous solution, a suspension, an emulsion, etc., a pill, a capsule, a granule or a tablet by additionally adding a diluent, a dispersant, a surfactant, a binder and/or a lubricant, and it can be used by binding a target organ-specific antibody or other ligand with the carrier.

Furthermore, it can be suitably formulated depending on the particular disease or ingredient by using appropriate methods in the art or using the methods disclosed in the Remington's literature (Remington's Pharmaceutical Science (newest edition), Mack Publishing Company, Easton Pa.). For example, it can be formulated into one of a suspension, a liposomal formulation, an emulsion, a tablet, a capsule, a gel, a syrup or a suppository.

The administration method of the pharmaceutical composition according to the present disclosure is not particularly limited and any known administration method of inhibitors may be applied. Depending on purposes, parenteral administration (e.g., intranasal, intravenous, subcutaneous, intraperitoneal or topical administration) or oral administration may be employed. Specifically, administration by intranasal injection may be selected to achieve a quick therapeutic effect.

Also, the pharmaceutical composition according to the present disclosure is administered in a pharmaceutically effective amount. The 'pharmaceutically or therapeutically effective amount' means an amount sufficient to treat a disease at a reasonable benefit/risk ratio applicable to medical treatment, and an effective dose level will depend on factors including the type and severity of the disease, the activity of a drug, sensitivity to the drug, the time of administration, the route of administration, the rate of excretion, the duration of the treatment, and drugs used together, and other factors well known in the medical field.

The pharmaceutical composition may be administered as an individual therapeutic agent or in combination with other therapeutic agents, sequentially or concurrently with conventional therapeutic agents, and may be administered singly or multiply. It is important that the pharmaceutical composition is administered in such an amount that the maximum effect can be obtained with a minimum amount without side effects considering all of the above-mentioned factors, which can be easily determined by those skilled in the art.

The dosage may vary depending on the patient's body weight, age, sex, health condition and diet, administration time, administration method, excretion rate, the severity of the disease, etc., and a proper dosage may also vary depending on the amount of the drug accumulated in the patient's body and/or the specific efficacy of the polynucleotide used. In general, it can be calculated on the basis of $EC_{50}$ measured as effective from an in-vivo animal model and in vitro. For example, it may be from 0.01 μg to 1 g per 1 kg of body weight, and may be administered once to several times per unit period in a daily, weekly, monthly, or annual unit period. Also, it can be administered continuously for a long period of time using an infusion pump. The number of repeated administrations is determined in consideration of the time during which the drug remains in the body, the drug concentration in the body, and the like. Even after treatment according to the course of disease treatment, the pharmaceutical composition can be continuously administered to prevent the recurrence of the disease.

In an exemplary embodiment, the present disclosure provides a method for screening a substance for treating or preventing Alzheimer's disease or a brain disease, which includes a step of contacting miR-485-3p with a test substance and a step of determining the activity of miR-485-3p in contact with the test substance, wherein the test substance is selected as a candidate substance if the activity of miR-485-3p in contact with the test substance is decreased as compared to the activity of miR-485-3p of a control group, not in contact with the test substance.

The miR-485-3p is provided in the form of a cell expressing the same, and the activity is analyzed as the expression level of miR-485-3p. For example, after contacting a cell expressing the miR-485-3p according to the present disclosure with test substances, the change in the expression level of miR-485-3p is compared with that before the contacting or with a control group cell not in contact with the test substances and the substance which shows change, particularly decrease, in the expression level is selected as a candidate substance. The expression level of miR-485-3p may be measured by performing a known method such as northern blot, RT-PCR, a hybridization method using a microarray, etc.

The miR-485-3p is provided in the form of a cell expressing the same, and the activity is determined by analyzing the interaction of the miR-485-3p with the 3'-UTR of its typical ELAVL2 protein (ELAV like neuron-specific RNA binding protein 2). For example, after contacting a cell expressing the miR-485-3p according to the present disclosure with test substances, the degree of interaction between the 3'-UTR of the ELAVL2 protein and miR-485-3p is compared with that before the contacting or with a control group cell not in contact with the test substances and the substance which shows change, particularly decrease, in the interaction is selected as a candidate substance. The RNA-RNA interaction used in the method according to the present disclosure may be detected by a method known in the art, for example, RNA walk (Lusting et al., *Nucleic Acids Res.* 2010; 38 (1): e5) or yeast two-hybrid system (Piganeau et al, *RNA* 2006; 12: 177-184, and RNA: A Laboratory Manual (Cold Spring Harbor Laboratory Press 2011)).

The type of cell and the amount and kind of the test substances used in the screening method will vary depending on the particular test method and test substances used, and those skilled in the art will be able to select the suitable type, amount and/or condition of the cell. Based on the test result, the substance which leads to decreased activity of miR-485-3p in the presence of the test substance as compared to the control group not in contact with the test substance is selected as the candidate substance. The decrease means decrease by about 99% or less, decrease by about 95% or less, decrease by about 90% or less, decrease by about 85% or less, decrease by about 80% or less, decrease by about 75% or less, decrease by about 70% or less, decrease by about 65% or less, decrease by about 60% or less, decrease by about 55% or less, decrease by about 50% or less, decrease by about 45% or less, decrease by about 40% or less, decrease by about 30% or less, or decrease by about 20% or less, as compared to the control group, although not being limited thereto.

The 'test substance' means a substance which is expected to inhibit the activity of miR-485-3p as described above, and includes a low-molecular-weight compound, a high-molecular-weight compound, a mixture of compounds (e.g., a natural extract or a cell or tissue culture), a biomedicine (e.g., a protein, an antibody, a peptide, DNA, RNA, an antisense oligonucleotide, RNAi, an aptamer, RNAzyme and DNAzyme), a sugar and a lipid, although not being limited thereto. The test substance can be a polypeptide having two or more amino acid residues, for example, 6, 10, 12, 20 or fewer, or more than 20, e.g., 50, amino acid residues. The test substance may be obtained from a library of synthetic or natural compounds, and a method for obtaining a library of such compounds is known in the art. The libraries of synthetic compounds are commercially available from Maybridge Chemical Co. (UK), Comgenex (USA), Brandon Associates (USA), Microsource (USA) and Sigma-Aldrich (USA), and the libraries of natural compounds are commercially available from Pan Laboratories (USA) and MycoSearch (USA). The test substance may be obtained by a variety of combinatorial library methods known in the art, for example, a biological library, a spatially addressable parallel solid-phase or solution-phase library, a synthetic library requiring deconvolution, a "one-bead/one-compound" library, and a synthetic library using affinity chromatography selection. Method for the synthesis of molecular libraries are disclosed in DeWitt et al., *Proc. Natl. Acad. Sci. U.S.A.* 90, 6909, 1993; Erb et al. *Proc. Natl. Acad. Sci. U.S.A.* 91, 11422, 1994; Zuckermann et al., *J. Med. Chem.* 37, 2678, 1994; Cho et al., *Science* 261, 1303, 1993; Carell et al., *Angew. Chem. Int. Ed. Engl.* 33, 2059, 1994; Carell et al., Angew. *Chem. Int. Ed. Engl.* 33, 2061; Gallop et al., *J. Med. Chem.* 37, 1233, 1994, or the like.

For the screening purpose of a drug which treats Alzheimer's disease and/or various brain diseases according to the present disclosure, a low-molecular-weight exhibiting a therapeutic effect may be used. For example, a compound with a molecular weight of about 1000 Da, e.g., 400 Da, 600 Da or 800 Da, may be used. Depending on purposes, these compounds can form a part of a compound library, and the number of compounds that make up the library can also vary from dozens to millions. The compound library may contain peptides, peptoids, other cyclic or linear oligomeric compounds, template-based low-molecular-weight compounds, e.g., benzodiazepines, hydantoins, biaryls, carbocycles and polycyclic compounds (e.g., naphthalene, phenothiazine, acridine, steroid, etc.), carbohydrates, amino acid derivatives, dihydropyridines, benzhydryls and heterocycles (e.g. triazine, indole, thiazolidine, etc.), although not being limited thereto.

In addition, a cell or a biomolecule may be used in the screening. The biomolecule refers to a protein, a nucleic acid, a carbohydrate, a lipid or a material produced in vivo or in vitro using a cellular system. The biomolecule may be provided either alone or in combination with other biomolecules or cells. For example, the biomolecule includes polynucleotides, peptides, antibodies or other proteins or biological organic materials found in the plasma.

In an exemplary embodiment, the present disclosure provides a method for detecting a miR-485-3p marker to provide information required for diagnosis or prognosis of various brain disease Alzheimer's disease and/or various brain diseases, which includes a step of detecting the expression of a miR-485-3p marker from a sample; and a step of associating the expression level of the detected marker with the diagnosis or prognosis of Alzheimer's disease and/or various brain diseases.

In the present disclosure, in the step of the association, the determined expression level of the marker is compared with the detection result for each of the marker determined for a control group. The miR-485-3p marker shows increased expression level as compared to the control group.

During the diagnostic or prognostic determination of Alzheimer's disease and/or various brain diseases, non-marker clinical information of the test subject may be used in addition to the expression level of the marker. The non-marker clinical information of the test subject includes the age, sex, body weight, diet, body mass, underlying diseases, brain waves, type of seizure, brain MRI, brain CT, cerebral spinal fluid test result, blood test result and saliva test result of the subject, although not being limited thereto.

The present disclosure is based on the finding that the excessive inhibition of the expression of the ELAVL2 protein by miR-485-3p is involved in the development of Alzheimer's disease and/or various brain diseases. In another exemplary embodiment, the present disclosure provides a method for treating or preventing Alzheimer's disease and/or a brain disease by inhibiting the activity of miR-485-3p in the cells or tissues, particularly in the brain cells, brain tissues or brain, of a subject.

In an exemplary embodiment, the present disclosure provides a method for treating or preventing Alzheimer's disease and/or a brain disease, which includes a step of administering a therapeutically or prophylactically effective amount of a miR-485-3p activity inhibitor to a subject in need of treatment or prevention of Alzheimer's disease and/or a brain disease.

Further, in an exemplary embodiment, the present disclosure provides a substance capable of inhibiting the activity of miR-485-3p for the purpose of treating or preventing a brain disease diseases. In particular, the substance capable of inhibiting the activity of miR-485-3p is delivered to the brain.

Reference can be made to the foregoing descriptions about the miR-485-3p activity inhibitor that can be used, the regulation or inhibition of the activity of miR-485-3p, the method of administration, the type of diseases that can be treated, etc.

Hereinafter, the present disclosure will be described in detail through examples. However, the following examples are for illustrative purposes only and it will be apparent to those of ordinary skill in the art that the scope of the present disclosure is not limited by the examples.

EXAMPLE 1: ANALYSIS OF MIRNA EXPRESSION PATTERN IN PLASMA OF ALZHEIMER'S PATIENTS Using miRNA qPCR Array (1) Patients and Sample Preparation Table 1 shows the characteristics of the patients used in the study. About 3 mL of blood was collected in blood tubes (Becton Dickinson, Germany) containing sodium citrate (3.2% w/v) from 4 patients diagnosed with Alzheimer's dementia by physicians. Four healthy adults of corresponding ages (±4 years) were included as a control group.

TABLE 1

Sex and age of normal group and patient group

| Group | Sample No. | Sex | Age |
|---|---|---|---|
| Normal group | N1 | Female | 78 |
| Normal group | N2 | Male | 72 |
| Normal group | N3 | Female | 74 |
| Normal group | N4 | Male | 79 |
| Patient Group | S1 | Female | 72 |
| Patient Group | S2 | Female | 82 |
| Patient Group | S3 | Female | 84 |
| Patient Group | S4 | Male | 75 |

The blood was centrifuged for 10 minutes at 3,500 rpm to separate plasma and then stored at −80° C. until RNA extraction. miRNA was extracted using the miRNAeasy Serum/Plasma kit (Qiagen, USA) according to the manufacturer's recommendations. The concentration and purity of the extracted RNA were analyzed using Bioanalyzer 2100 (Agilent, USA). Eight groups including a normal group satisfied the quality criteria and were used in the study.

(2) miRNA qPCR Array

The genes used in miRNA qPCR array assay are listed in Table 2. The mature sequence of each miRNA is available from the miRNA database (http://www.mirbase.org). The extracted RNA was screened using the miRNA array containing 84 different miRNAs known to be associated with human neurological development and the progress of neurological disease.

TABLE 2

List of genes used in miRNA qPCR array assay

| No. | Mature miRNA list |
|---|---|
| 1 | hsa-let-7b-5p |
| 2 | hsa-let-7c-5p |
| 3 | hsa-let-7d-5p |
| 4 | hsa-let-7e-5p |
| 5 | hsa-let-7i-5p |
| 6 | hsa-miR-101-3p |
| 7 | hsa-miR-105-5p |
| 8 | hsa-miR-106b-5p |
| 9 | hsa-miR-107 |
| 10 | hsa-miR-124-3p |
| 11 | hsa-miR-125b-5p |
| 12 | hsa-miR-126-5p |
| 13 | hsa-miR-128-3p |
| 14 | hsa-miR-130a-3p |
| 15 | hsa-miR-132-3p |
| 16 | hsa-miR-133b |
| 17 | hsa-miR-134-5p |
| 18 | hsa-miR-135b-5p |
| 19 | hsa-miR-138-5p |
| 20 | hsa-miR-139-5p |
| 21 | hsa-miR-140-5p |
| 22 | hsa-miR-146a-5p |
| 23 | hsa-miR-146b-5p |
| 24 | hsa-miR-148b-3p |
| 25 | hsa-miR-151a-3p |
| 26 | hsa-miR-152-3p |
| 27 | hsa-miR-15a-5p |
| 28 | hsa-miR-15b-5p |
| 29 | hsa-miR-181a-5p |
| 30 | hsa-miR-181d-5p |
| 31 | hsa-miR-191-5p |
| 32 | hsa-miR-193b-3p |
| 33 | hsa-miR-195-5p |
| 34 | hsa-miR-19b-3p |
| 35 | hsa-miR-203a-3p |
| 36 | hsa-miR-20a-5p |
| 37 | hsa-miR-212-3p |
| 38 | hsa-miR-22-3p |
| 39 | hsa-miR-24-3p |
| 40 | hsa-miR-26b-5p |
| 41 | hsa-miR-27a-3p |
| 42 | hsa-miR-28-5p |
| 43 | hsa-miR-298 |
| 44 | hsa-miR-29a-3p |
| 45 | hsa-miR-29b-3p |
| 46 | hsa-miR-29c-3p |
| 47 | hsa-miR-302a-5p |
| 48 | hsa-miR-302b-5p |
| 49 | hsa-miR-30d-5p |
| 50 | hsa-miR-320a |
| 51 | hsa-miR-328-3p |
| 52 | hsa-miR-337-3p |
| 53 | hsa-miR-338-3p |
| 54 | hsa-miR-339-5p |
| 55 | hsa-miR-342-3p |
| 56 | hsa-miR-346 |
| 57 | hsa-miR-34a-5p |
| 58 | hsa-miR-376b-3p |
| 59 | hsa-miR-381-3p |
| 60 | hsa-miR-409-3p |
| 61 | hsa-miR-431-5p |
| 62 | hsa-miR-432-5p |
| 63 | hsa-miR-433-3p |
| 64 | hsa-miR-455-5p |
| 65 | hsa-miR-484 |
| 66 | hsa-miR-485-3p |
| 67 | hsa-miR-485-5p |
| 68 | hsa-miR-487a-3p |
| 69 | hsa-miR-488-3p |
| 70 | hsa-miR-489-3p |
| 71 | hsa-miR-499a-5p |
| 72 | hsa-miR-509-3p |
| 73 | hsa-miR-511-5p |
| 74 | hsa-miR-512-3p |
| 75 | hsa-miR-518b |
| 76 | hsa-miR-539-5p |
| 77 | hsa-miR-652-3p |
| 78 | hsa-miR-7-5p |
| 79 | hsa-miR-9-5p |
| 80 | hsa-miR-9-3p |
| 81 | hsa-miR-92a-3p |
| 82 | hsa-miR-93-5p |
| 83 | hsa-miR-95-3p |
| 84 | hsa-miR-98-5p |

The Quantitative PCR assay method can be summarized as follows. A mature miRNA is generally a 22-nucleotide, non-coding RNA and is responsible for post-transcriptional regulation. Polyadenylation of mature miRNA was induced by poly(A) polymerase, and cDNA was synthesized using oligo-dT primers. The oligo-dT primer enables the amplification of the mature miRNA during the real-time PCR process because it has a 3' degenerate anchor and a universal tag sequence at the 5' end. The mature miRNA was quantified during the real-time PCR process using the miScript SYBR Green PCR kit (Qiagen).

(3) Analysis of miRNA Expression Pattern Through Volcano Plot

FIG. 1A shows a miRNA expression pattern analysis result (volcano plot) for the patient group as compared to the normal group. The expression pattern of 84 miRNAs was analyzed as compared to the normal group.

Figure 1B:
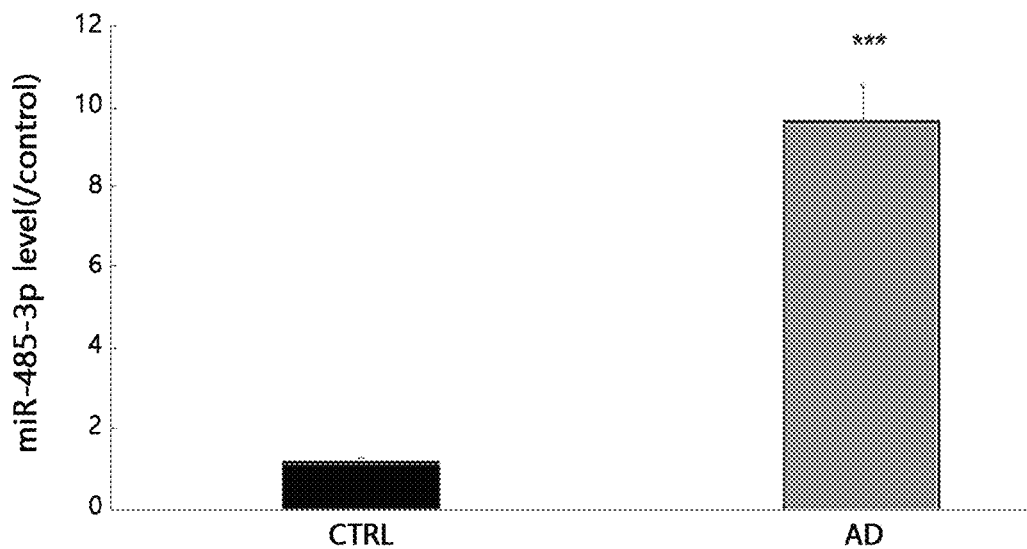

The x axis represents fold-change and the y axis represents −log 10 of the p value. The horizontal black line shows where the p value is 0.05 or smaller. As a result of the volcano plot analysis, it was confirmed that the expression of hsa-miR-105-5p, hsa-miR-98-5p, hsa-miR-15a-5p, hsa-miR-134-5p, hsa-miR-409-3p, hsa-miR-19b-3p, hsa-miR-92a-3p, hsa-miR-28-5p, hsa-miR-30d-5p, hsa-miR-212-3p, hsa-miR-93-5p, hsa-miR-342-3p, hsa-miR-381-3p, hsa-miR-431-5p, hsa-miR-130a-3p, hsa-miR-146b-5p, hsa-miR-29a-3p, hsa-miR-132-3p, hsa-miR-376b-3p, hsa-miR-22-3p, hsa-miR-509-3p, hsa-miR-139-5p, hsa-miR-499a-5p, hsa-miR-203a-3p, hsa-miR-95-3p, hsa-miR-128-3p, hsa-miR-487a-3p, hsa-miR-485-3p, hsa-miR-195-5p, hsa-miR-433-3p, hsa-miR-133b, hsa-miR-191-5p, hsa-miR-489-3p, hsa-miR-432-5p, hsa-miR-29c-3p, hsa-miR-485-5p, hsa-miR-652-3p, hsa-miR-126-5p, hsa-miR-328-3p, hsa-let-7b-5p, hsa-miR-539-5p, hsa-miR-106b-5p, hsa-miR-101-3p, hsa-miR-302a-5p, hsa-miR-484, hsa-miR-518b, hsa-miR-148b-3p, hsa-miR-181d-5p, hsa-miR-7-5p, hsa-miR-512-3p, hsa-miR-151a-3p, hsa-miR-15b-5p, hsa-let-7e-5p, hsa-miR-135b-5p, hsa-miR-181a-5p, hsa-miR-138-5p, hsa-miR-34a-5p, hsa-miR-346, hsa-miR-511-5p, hsa-miR-485-3p, hsa-miR-485-5p, hsa-miR-487a-3p, hsa-miR-489-3p, hsa-miR-499a-5p, hsa-miR-509-3p, hsa-miR-511-5p, hsa-miR-512-3p, hsa-miR-518b, hsa-miR-539-5p, hsa-miR-652-3p, hsa-miR-7-5p, hsa-miR-92a-3p, hsa-miR-93-5p hsa-miR-95-3p and hsa-miR-98-5p was increased in the patient group. However, the regulation of miRNA was not statistically significant except for hsa-miR-485-3p. The expression of hsa-485-3p was significantly increased in the Alzheimer's patients as compared to the normal group, with a p value of 0.00439. The expression level was different by about 9-fold for severe dementia as compared to the normal group with 1-fold. The intermediacy between 1-fold and 9-fold can be distinguished as mild cognitive impairment (FIG. 1B). Therefore, hsa-miR-485-3p can be used as a marker for diagnosis of Alzheimer's disease.

EXAMPLE 2: PREDICTION OF HUMAN MIRNA TARGET GENE, CONSERVATION OF SAME MIRNA TARGET GENE IN MOUSE AND SYNTHESIS OF ANTI-MMU-MIR-485-3P

In order to analyze the base sequence and target location of hsa-miR-485-3p, it was confirmed using a target prediction software (miRDB) that the 3'-untranslated region (UTR) of human-derived ELAVL2 is the target of hsa-miR-485-3p. It was confirmed that the identified seed sequence was conserved also in mmu-miR-485-3p and the 3'-untranslated region of mouse-derived ELAVL2.

FIG. 2 shows a list of the 3'-untranslated region (UTR) mRNAs of ELAVL2 known as a target known of hsa-miR485-3p, and shows the 3'-untranslated region (UTR) mRNAs of target ELAVL2 of miR485-3p. The 5' seed sequence of miR-485-3p (ELAVL2) is shown in red color. Table 3 shows the base sequence of has-miR-485-3p. A functional study was conducted to elucidate the physiological functions of miR-485-3p using an Alzheimer's disease model by synthesizing the sequence.

TABLE 3

| Base sequence of hsa-miR485-3p | | |
|---|---|---|
| Gene | Sequence (5'→3') | SEQ ID NO |
| hsa-miR485-3p | GUCAUACACGGCUCUCCUCUCU | 1 |

Table 4 shows the results of analyzing the base sequence and target location of mmu-miR485-3p. It was confirmed using target prediction softwares (TargetScan, PicTar, and microT) that the 3'-untranslated region (UTR) of mouse ELAVL2 mouse and the target sequence of mmu-miR-485-3p were conserved. It was confirmed that the 3'-untranslated region (UTR) of mouse ELAVL2 is the target of mmu-miR-485-3p.

TABLE 4

| Analysis of base sequence and target location of mmu-miR485-3p | | | |
|---|---|---|---|
| Gene | Sequence(5'->3') | | SEQ ID NO |
| mmu-miR-485-3p | AGUCAUACACGGCUCUCCCUCUC | | 8 |
| Target gene | Gene name | 3P-seq Total tags + 5 sites | Representative miRNA |
| ELAVL2 | ELAV like neuron-specific RNA binding protein 2 | 78　　3 | mmu-miR-485-3p |

For the mmu-miR-485-3p overexpressed in the Alzheimer's disease mouse model, an antisense oligonucleotide modified with a target gene associated with Alzheimer's and a brain disease, a specific sequence antagomir, 2'-O-methylation and phosphorothioate was synthesized.

EXAMPLE 3: ANALYSIS OF MIR-485-3P EXPRESSION IN HIPPOCAMPUS AND CEREBRAL CORTEX OF 5×FAD MOUSE (RT-QPCR)

(1) Research Methods

5×FAD transgenic mouse is an animal model of Alzheimer disease obtained by overexpressing mutant forms of APP and PSEN1, which exhibits severe accumulation of intraneuronal Aβ42 from about 6 weeks.

Given the result of Example 1, RT-qPCR was performed to confirm the expression of miR-485-3p in the dementia animal model. 10-month-old 5×FAD transgenic mouse and wild-type (WT) mouse were deeply anesthetized and sacrificed by decapitation. After excising the brain immediately, the hippocampus and cerebral cortex were dissected from the remaining brain structure. Total miRNA was isolated from the hippocampus using the PAXgene Tissue miRNA kit (Qiagen, USA) according to the manufacturer's instructions. cDNA was synthesized using the miScript II RT kit (Qiagen, USA), and qPCR was performed using the mmu_miR-485-3p miScript Primer Assay kit and the miScript SYBR Green PCR kit. The miRNA level was quantified by normalizing to snoRNA202 (control mouse).

(2) Research Results

FIG. 3A compares the expression of miR-485-3p in the hippocampus and the cortex. RT-PCR was conducted to investigate the expression pattern of miR-485-3p in the hippocampus and the cerebral cortex of 5×FAD. The result showed that the expression of miR-485-3p was increased in the hippocampus of 5×FAD as compared to wild-type (WT). This, together with the results of Example 1, shows that the expression of miR-485-3p is increased in Alzheimer's dementia. Therefore, the neuronal target mRNA or protein that may be affected by miR-485-3p was investigated.

EXAMPLE 4: CONFIRMATION OF EXPRESSION OF RELATED PROTEINS INCLUDING ELAVL2 AND AMYLOID BETA 42 PROTEIN IN HIPPOCAMPUS AND CEREBRAL CORTEX OF 5×FAD MOUSE (1) Research Methods Given the results of Example 3, the expression of related proteins including ELAVL2 and the amyloid beta42 protein in the hippocampus and the cerebral cortex of 5×FAD was investigated. After sacrificing an anesthetized mouse (9-month-old) by decapitation, the brain was extracted immediately. After preparing a homogenate of the brain (hippocampus and cerebral cortex), western blot was conducted using an anti-ELAVL2 antibody (Abcam, USA), a cFOS antibody (Cell Signaling, USA), an APP antibody (Cell Signaling, USA) and an amyloid beta antibody (Cell Signaling, USA). The immunoreactive protein was visualized with a chemiluminescence reagent (GE Healthcare, UK) and was measured and quantified using a chemiluminescence analyzer (Fusion SL). The amyloid beta 42 protein in the hippocampus and the cerebral cortex was quantified by using the mouse/rat amyloid beta (1-42) ELISA kit (IBL) according to the manufacturer's instructions.

(2) Research Results

1) Confirmation of ELAVL2 Expression in Hippocampus and Cerebral Cortex

FIG. 3B and FIG. 3C show the result of comparing the expression of ELAVL2 and related proteins in the hippocampus and the cerebral cortex of 5×FAD. ELAVL2, an ELAV-like RNA-binding to protein, is known as a protein that regulates neural functions such as neuronal excitation or synaptic transmission, which are directly associated with cognitive and behavioral functions. Also, ELAVL2 is responsible for post-transcriptional gene regulation as a neural-specific RNA-binding protein by recognizing the GAAA motif of RNA. As its target, the transcription factor cFOS which affects the expression level of the protein is known. Also, cFOS is known to influence the expression of the APP protein, which is known as an amyloid beta precursor in brain cells. It was confirmed that the increase pattern of miR-485-3p significantly affects the expression level of APP.

2) Comparison of Aβ42 Expression in Cerebral Cortex and Hippocampus

Figure 4A:
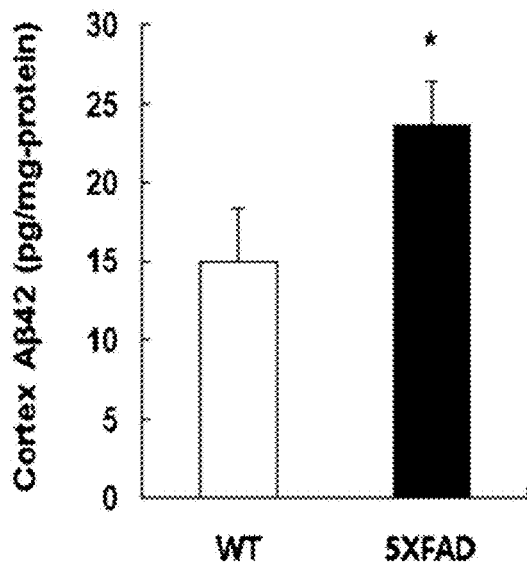
FIGS. 4A-4B show a graph showing a comparative quantitative analysis result of Aβ 42 in the cerebral cortex of 5xFAD (FIG. 4A), and a comparative quantitative analysis result of AO 42 in the hippocampus (FIG. 4B).
Figure 4B:
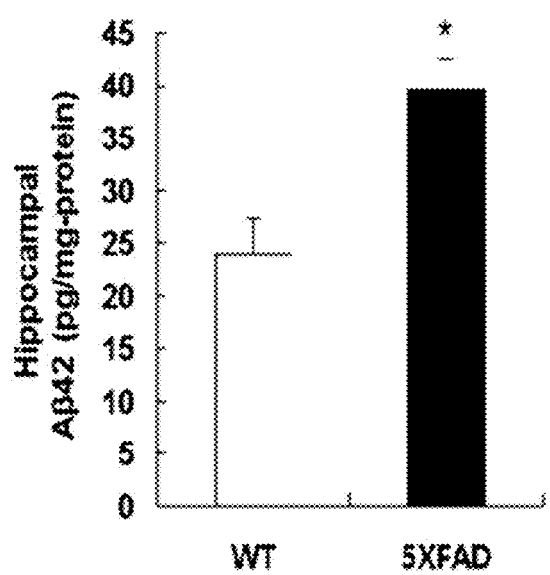

FIGS. 4A-4B show results of quantitatively comparing the expression of Aβ42 in the cerebral cortex and the hippocampus of 5×FAD. It was confirmed that Aβ42 was significantly increased as compared to WT both in the cerebral cortex (FIG. 4A) and in the hippocampus (FIG. 4B) of 5×FAD. Based on this result, it can be seen that the regulation of miR-485-3p can be a way to reduce amyloid beta, which known as the causative agent of Alzheimer's disease.

EXAMPLE 5: MEASUREMENT OF AMYLOID BETA (Aβ) 42 ISOLATED FROM SALIVA (1) Research Methods The measurement of amyloid beta in saliva is advantageous in that the accuracy is better than for blood because of the proximity to the brain and early diagnosis is possible because even a small amount of amyloid beta can be quantified. In addition, a higher accuracy (≥99%) can be ensured by doubly checking blood, miRNA, etc.

Figure 5:
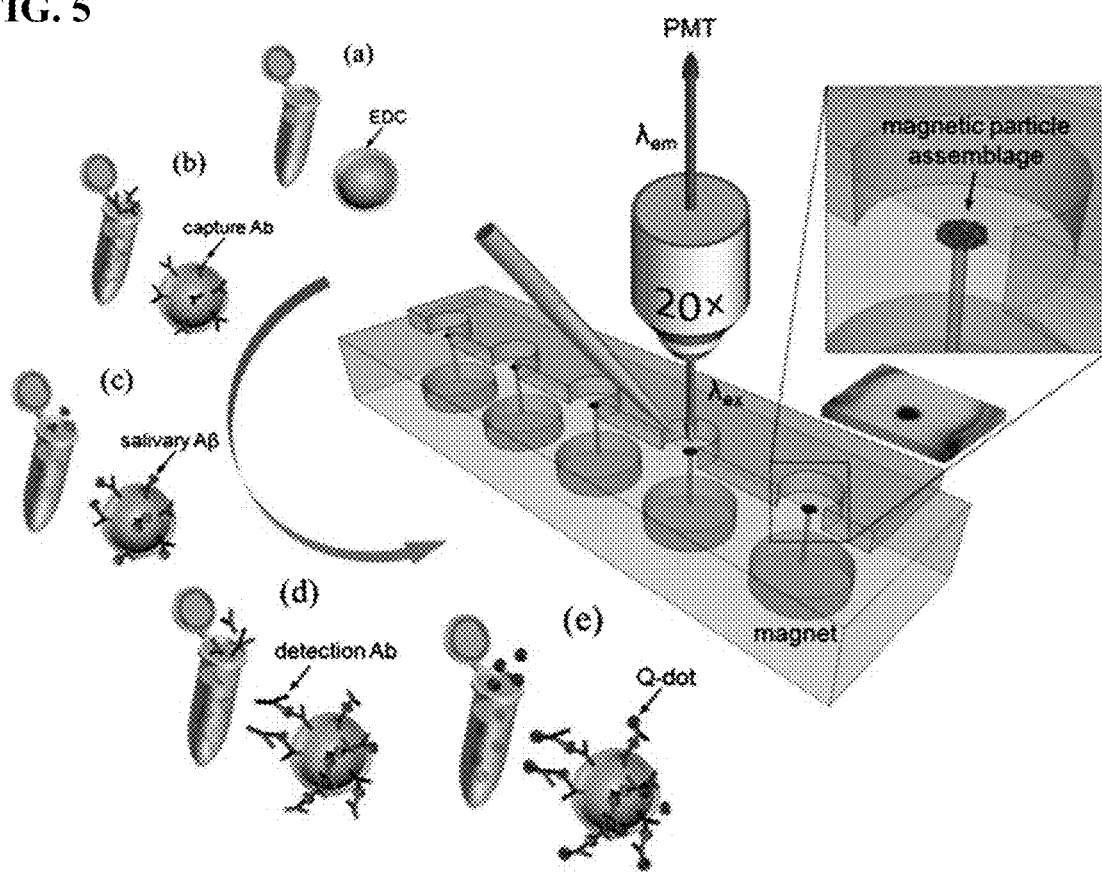
FIG. 5 is a schematic diagram of a magnetic particle collection device. A process wherein an antigen, an antibody, a magnetic particle and a fluorescent material form a complex is shown.
Figure 7A:
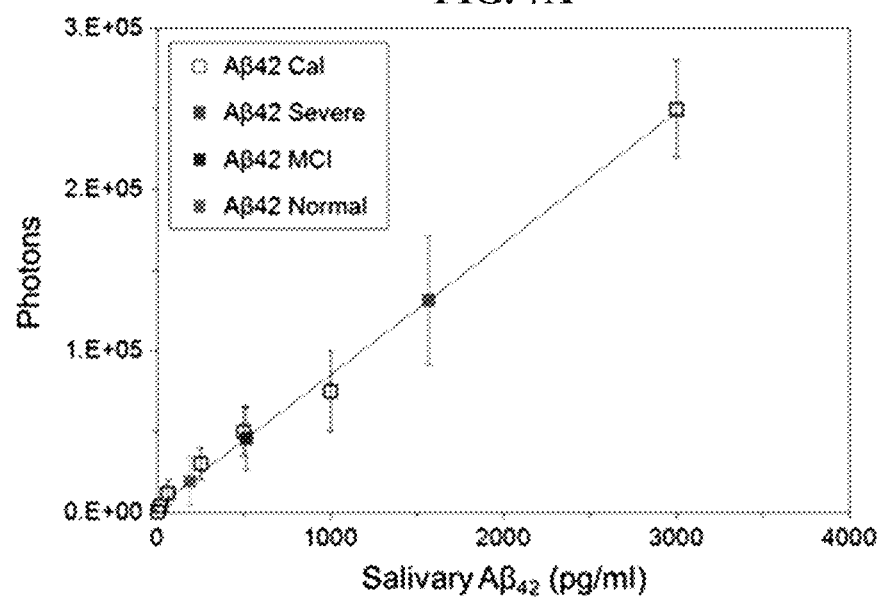
FIGS. 7A-7D show that a dementia patient can be distinguished by measuring the concentration of saliva-derived Aβ using a magnetic particle collection device.
Figure 7B:
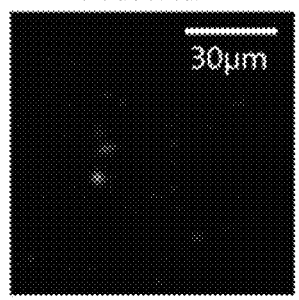
Figure 7C:
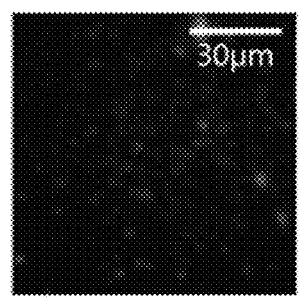
Figure 7D:
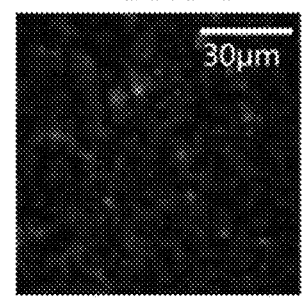
Figure 8:
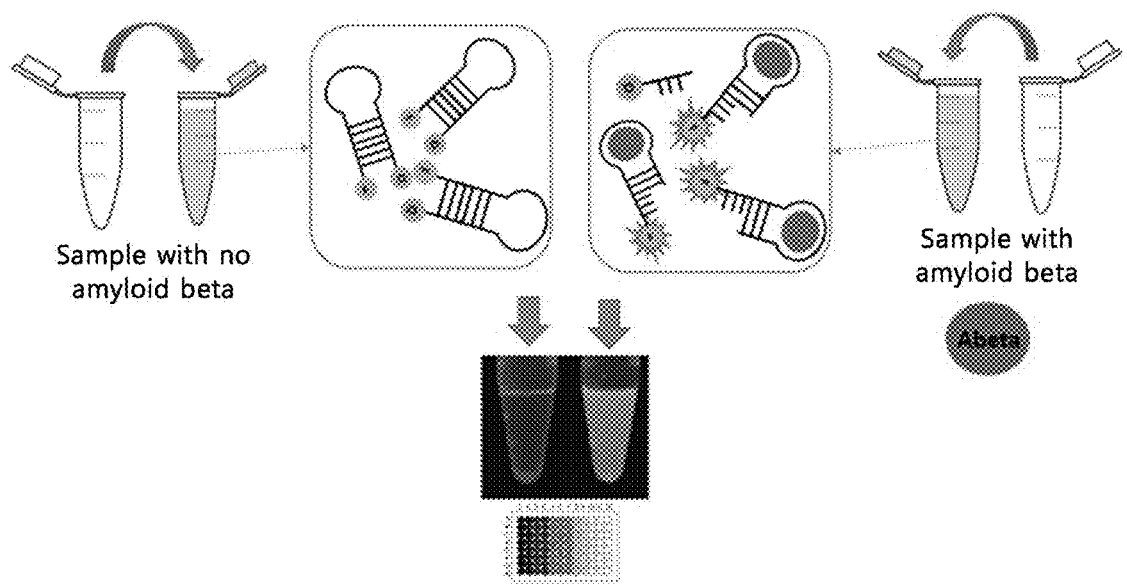
FIG. 8 is a schematic diagram of a process of measuring the level of a nucleic acid expressing amyloid beta (Aβ) 42.

A multi-nucleic acid having the structural features that, upon binding to amyloid beta 42, fluorescence is emitted as a quencher is detached at the same time was synthesized by using a sequence binding specifically to amyloid beta 42 and a sequence self-coupled within the nucleic acid. Because the size of the multi-nucleic acid is smaller than an antibody, its specificity and selectivity are excellent. Also, because sampling and large-scale analysis are possible within one hour, it can provide a diagnostic method with high diagnostic ease. The amyloid beta 42 in saliva was quantified by using the platform technology (magnetic immunoassay system) which can assemble a very small amount of a biomarker as a monolayer (FIG. 5). The assemblage of nanoparticles on a specified area could be achieved. The aggregate of the complex of the saliva-derived amyloid beta and the magnetic particle was 300 μm or smaller in diameter, and the number of the magnetic particles in the aggregate was $\sim 1.0 \times 10^4$ (FIG. 6A). The region of interest (ROI) in photomultiplier tube (PMT) analysis was $100 \times 100$ μm$^2$. The fluorescent substances was measured 3 times using the PMT, and then the average value was calculated for each sample (FIG. 6B).

A normal group of 100 people and a patient group of 100 patients from mild cognitive impairment to severe dementia were recruited. Their ages ranged from early 30s to late 80s. The patients with other diseases that can affect dementia were excluded.

(2) Research Results

A trace amount of amyloid beta in saliva, which was not detectable by ELISA, could be measured. As a result of comparing with commercially available ELISA, amyloid beta was not detected for the normal subjects in their 30s.

The magnetic immunoassay system used in this example can easily detect the amyloid beta peptide in saliva at a slightly high concentration of ~20 pg/mL as compared to the commercially available ELISA system. According to the protocol of the ELISA system used, the lowest measurable concentration of the standard amyloid beta peptide is 7.4 pg/mL, which can be a little ambiguous because the curve fitting for measurement cannot meet the exact linearity in very low concentration ranges.

As a result of measuring saliva-derived amyloid beta 42 for the dementia patients, it was possible to distinguish normal cases, mild cognitive impairment (MCI) and severe cases. The concentration of beta amyloid was 0-500 pg/mL for normal cases, 500 pg to 1 ng/mL for mild cognitive impairment, and 1 ng/mL or higher for severe cases (FIGS. 7A-7D). In addition, the amyloid beta level of over 100 dementia patients was normalized, and mild cognitive impairment and moderate dementia could be distinguished successfully (90% or higher match with diagnosis by clinicians).

EXAMPLE 6: PREPARATION AND IN-VITRO TRANSFECTION OF HIPPOCAMPAL PRIMARY CELL LINE (1) Research Methods Primary cells derived from the tissues of the hippocampus and the cerebral cortex excised from the embryo of 5×FAD were cultured. The methods for cell preparation and culture followed the previous research (Seibenhener, M. L & Woonten M. W, Isolation and culture of Hippocampal Neurons from Prenatal Mice, Jove, 2012). 50 nM of miR-485-3p duplex (or scrambled miRNA duplex; Bioneer, Daejon, South Korea) and 50 nM of antagomir (AM) 485-3p were transfected into primary cells in vitro using Lipofectamine 2000. A cell homogenate was obtained 48 hours after the transfection, which was subjected to western blot using ELAVL2 antibody (Abcam, UK). The immunoreactive protein was visualized with a chemiluminescence reagent (GE Healthcare, UK) and was measured and quantified using a chemiluminescence analyzer (Fusion SL). The amyloid beta 42 protein was measured by using the mouse/rat amyloid beta (1-42) ELISA kit (IBL) according to the manufacturer's instructions.

(2) Research Results

Figure 9A:
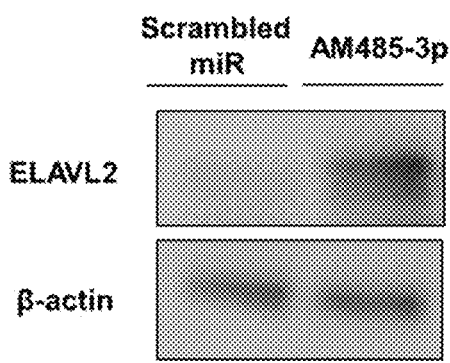
FIGS. 9A-9B are images of a gel electrophoresis (FIG. 9A) and a bar graph (FIG. 9B) showing results of comparing the expression of ELAVL2 in hippocampal primary cells transfected with AM485-3p.
Figure 9B:
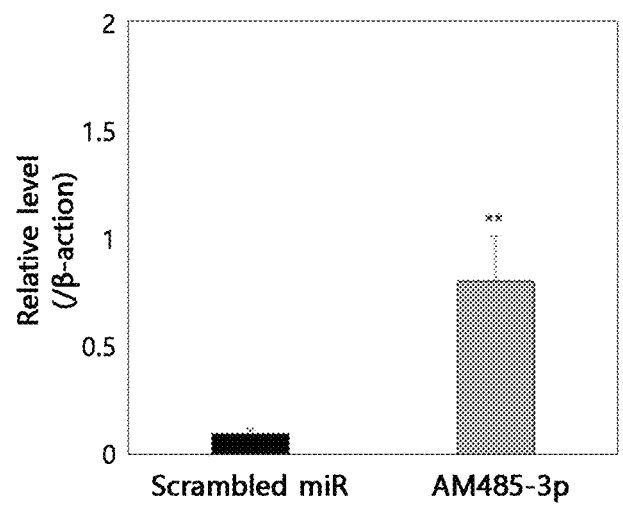

The expression of ELAVL2 in the hippocampal primary cells depending on the transfection with AM485-3p (2'-O-methylated)-5'-gagaggagagccguguaugacu-3' (SEQ ID NO 9)) was compared (FIGS. 9A-9B). It was confirmed that ELAVL2 was expressed in the hippocampal primary cells of 5×FAD, and the expression of ELAVL2 expression was increased in the cells transfected with AM485-3p as compared to the control. This means that miR-485-3p inhibits the expression of ElAVL2 in the cells treated with AM485-3p. Because ELAVL2 is an important factor affecting cognitive function by being involved in excitation of neurons, the development of a drug or a composition that increases ELAVL2, such as a miR-485-3p inhibitor, can be a key strategy in preventing/treating of Alzheimer's disease.

EXAMPLE 7: COMPARATIVE QUANTIFICATION OF RELATED PROTEINS INCLUDING ELAVL2 AMYLOID BETA 42 PROTEIN IN 5×FAD INTRANASALLY TREATED WITH AM485-3P (1) Research Methods The inhibition of miR-485-3p was induced by intranasally administering a sequence-specific antagomir or a scrambled sequence antagomir. The intranasal administration of the antagomir carried out according to a method targeting the brain without anesthetizing in the mouse (Leah R. T., et al. (2013) Intranasal Administration of CNS Therapeutics to Awake Mice. *J Vis Exp.* 2013; (74): 4440). After immobilizing the accustomed mouse for intranasal inhalation (intranasal grip) and positioning so that the abdomen faces upward, a pipette was positioned in front of one nasal cavity. 6 μL was inhaled dropwise twice using the pipette (1 drop=3 μL). After maintaining the position for 15 seconds, intranasal inhalation into the right nasal cavity was conducted in the same manner. The same procedure was repeated 2 minutes later. A total of 24 μL was inhaled (AM485 (2'-O-methylated)-5'-gagaggagagccguguaugacu-3' (SEQ ID NO 9); 5 nmol in 24 μL of distilled water treated with 0.1% v/v diethylpyrocarbonate; Bioneer, Korea). A vehicle of the same volume was administered to a control mouse. 12 weeks after the nasal administration (once a week), the anesthetized mouse was sacrificed by decapitation and the brain was excised immediately. After preparing a homogenate of the brain (hippocampus and cerebral cortex), western blot was conducted using anti-ELAVL2 antibody (Abcam, USA), cFOS antibody (Cell Signaling, USA), APP antibody (Cell Signaling, USA) and amyloid beta antibody (Cell Signaling, USA). The immunoreactive protein was visualized with a chemiluminescence reagent (GE Healthcare, UK) and was measured and quantified using a chemiluminescence analyzer (Fusion SL). The amyloid beta 42 protein was measured by using the mouse/rat amyloid beta (1-42) ELISA kit (IBL) according to the manufacturer's instructions.

(2) Research Results

The related proteins including ELAVL2 and the amyloid beta 42 protein were quantitatively compared for the 5×FAD intranasally treated with AM485-3p ((2'-O-methylated)-5'-gagaggagagccguguaugacu-3' (SEQ ID NO 9); FIGS. 10A-10C). Because it was confirmed in Example 6 that the treatment of a mouse primary cell line with AM485-3p induces change in ELAVL2, the effect of AM485-3p in vivo was investigated intranasally treating 5×FAD with AM485-3p. The ELAVL2 group showed increased expression of AM485-3p as compared to the control group. With the recovery of ELAVL2, the expression of cFOS, which is a transcription factor involved in APP expression, was normalized and this led to the decreased expression of APP, resulting in decrease in the amyloid beta 42 protein (FIGS. 10A and 10B). This suggests that the development of a drug such as a miR-485-3p inhibitor or a composition thereof is a key strategy in preventing/treating Alzheimer's disease. In addition, since it was confirmed in the animal model that the treatment with AM485-3p affects the inhibition of Aβ42 production (FIG. 10C), it seems that treatment with the related inhibitor or drug can relieve the pathological symptoms of Alzheimer's dementia.

EXAMPLE 8: COMPARISON OF COGNITIVE FUNCTION OF 5×FAD MOUSE INTRANASALLY TREATED WITH AM485-3P (1) Research Methods Y-maze and passive avoidance tests were carried out to investigate whether the intranasal treatment of AM485-3p (2'-O-methylated)-5'-gagaggagagccguguaugacu-3' (SEQ ID NO 9)) improved the cognitive function of 5×FAD.

1) Y-Maze Test

A Y-maze test apparatus is composed of Y-shaped maze prepared with black acrylic plates (10 cm wide, 41 cm long, 25 cm high). The maze is arranged with an angle of 120°. After dividing each maze into A, B and C zones, the experimental animals were placed carefully in each zone and allowed to move freely for 8 minutes. Spontaneous alternation (%) was evaluated by measuring the number and sequence of entries to each maze. The entrance into the three different zones in sequence was given one point (actual alternation, e.g., A-B-C, B-C-A, C-A-B, etc.). No point was given to discontinuous entrance. The spontaneous alternation (%) was calculated by the following formula.

% Spontaneous alteration=total number of alternation/(total number of entries−2)×100

2) Passive Avoidance Test

The passive avoidance test passive is a widely used method for measuring the working memory ability of rodents. A passive avoidance test apparatus is a shuttle box divided into two chambers, one equipped with a light bulb to create a bright environment that the test animals dislike, and the other with light blocked to create an environment which is comfortable for the animals. After two hours of stress application, the passive avoidance response was tested (training test). Aluminum grids were placed on the floor of the dark chamber at regular intervals so as to apply electric shocks to the sole of the animals. The experimental animals tend to enter the dark chamber. After keeping the animal in the bright chamber and then allowing to enter the dark chamber, electric shock (5 V, 0.5 mA, 10 sec) was applied so that it could remember it. 24 hours later, the time (latency time) lapsed until the entry into the dark chamber was measured up to 90 seconds without applying electric shock (retention tests 1, 2 and 3).

(2) Research Results

Figure 11A:
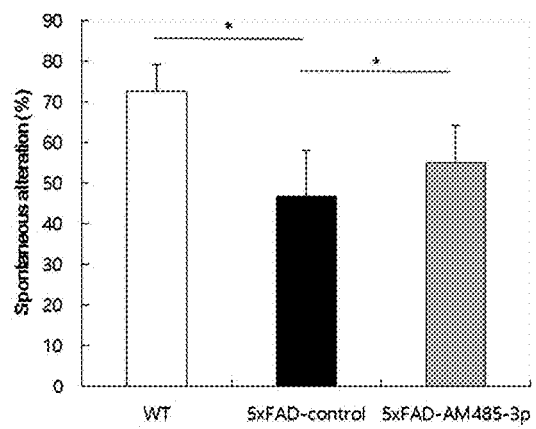
FIGS. 11A-11B show graphs comparing the cognitive function of 5xFAD intranasally treated with AM485-3p.
Figure 11B:
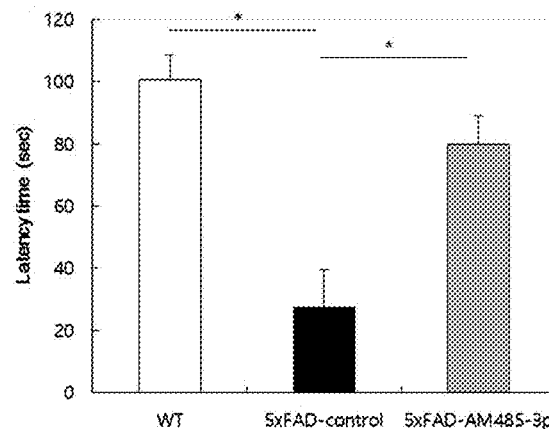

The cognitive function of the 5×FAD intranasally treated with AM485-3p (2'-O-methylated)-5'-gagaggagagccguaugacu-3' (SEQ ID NO 9)) was compared (FIGS. 11A-11B. As a result, both the spontaneous alteration (FIG. 11A) and the latency time (FIG. 11B) were decreased in 5×FAD as compared to WT. Because the typical symptoms of Alzheimer's dementia are behavior disorder and memory decline, the behavior disorder of 5×FAD seems to be due to the excessive accumulation and pathology of amyloid beta. However, the group intranasally treated with AM485-3p showed significant increase in both the spontaneous alteration and the latency time as compared to 5×FAD. It means that the treatment with AM485-3p can improve the main symptoms of Alzheimer's by relieving the pathological symptoms such as behavioral disorder and memory decline caused by the production of the amyloid beta42 protein facilitated by miR-485-3p. Therefore, the preparation of a drug that regulates miR-485-3p manufacturer or a composition thereof can be a new strategy to improve the main symptoms of Alzheimer's dementia, i.e., behavioral disorder and cognitive function.

EXAMPLE 9: STATISTICAL ANALYSIS

Two groups were compared by the Student's t-test, and three or more groups were compared by the Krushall-Wallis test. When the P value obtained from the Krushall-Wallis test was <0.05, two groups were tested post-hoc by the Mann-Whitney U test. P value of 0.05 or smaller for the two-tailed test was considered statistically significant.

According to the present disclosure, objective data analysis for diagnosis of Alzheimer's disease or a brain disease is possible by measuring the expression level of miR-485-3p in blood, the risk of a patient can be minimized by measuring the concentration of amyloid beta 42 in saliva, and fast and accurate diagnosis is possible. Therefore, the present disclosure is very useful in preventing Alzheimer's disease or a brain disease by diagnosing the Alzheimer's disease or the brain disease early.

While the specific embodiments of the present disclosure have been described in detail above, those skilled of ordinary skill in the art will appreciate that the specific embodiments are merely specific exemplary embodiments and the scope of the present disclosure is not limited by them. It is to be understood that the substantial scope of the disclosure is defined by the appended claims and their equivalents.

The invention claimed is:

1. A method of treating Alzheimer's disease in a subject in need thereof, comprising measuring the expression level of miR-485-3p in a sample from the subject, and administering a therapeutically effective amount of a nucleic acid complementary to miR-485-3p to the subject that is identified as having a high level of miR-485-3p, as compared to a control group.

2. The method of claim 1, wherein the sample is a blood sample.

3. The method of claim 1, wherein the expression level of miR-485-3p is measured by real-time PCR, quantitative PCR, primer extension, nucleic acid chip analysis, sequencing, aptamer-based assay, gel electrophoresis, or any combination thereof.

4. The method of claim 1, wherein the high level of miR-485-3p is characterized as a level of miR-485-3p that is 5 times or higher than the level of miR-485-3p in a control group.

5. The method of claim 1, wherein the high level of miR-485-3p is characterized as a level of miR-485-3p that is 9 times or higher than the level of miR-485-3p in a control group.

6. The method of claim 1, which further comprises measuring a concentration of amyloid beta 42 (A1342) in the sample.

7. The method of claim 6, wherein the sample is a saliva sample or a blood sample.

8. The method of claim 6, wherein the subject is identified as having a mild cognitive impairment (MCI) if the concentration of amyloid beta 42 is 500 pg/mL or higher and 1 ng/mL or lower.

9. The method of claim 6, wherein the subject is identified as having a severe cognitive impairment if the concentration of amyloid beta 42 is 1 ng/mL or higher.

10. The method of claim 1, wherein the miR-485-3p is the sequence as set forth in SEQ ID NO: 1 or SEQ ID NO: 2.

11. The method of claim 1, wherein the nucleic acid complementary to miR-485-3p has 15-30 nucleotides.

12. The method of claim 1, wherein the nucleic acid complementary to miR-485-3p comprises the sequence as set forth in SEQ ID NO: 3, 4, 5, 6, or 7.

13. The method of claim 1, wherein the nucleic acid complementary to miR-485-3p consists of the sequence as set forth in SEQ ID NO: 7.

14. The method of claim 1, wherein the nucleic acid complementary to miR-485-3p is a single stranded nucleic acid sequence.

15. The method of claim 1, wherein the nucleic acid complementary to miR-485-3p comprises a nucleotide analog.

16. The method of claim 15, wherein the nucleotide analog comprises PNA, LNA, 2'-O-methylated or methoxylated, or any combination thereof.

17. The method of claim 1, wherein the backbone of the nucleic acid complementary to miR-485-3p comprises phosphothioate.

18. The method of claim 1, wherein the nucleic acid complementary to miR-485-3p is formulated in a pharmaceutical composition comprising a pharmaceutically acceptable carrier.

19. The method of claim 18, wherein the nucleic acid complementary to miR-485-3p comprises the sequence as set forth in SEQ ID NO: 7.

* * * * *